United States Patent
Dien et al.

(10) Patent No.: US 7,306,933 B2
(45) Date of Patent: Dec. 11, 2007

(54) METHOD FOR PRODUCING L-LYSINE OR L-THREONINE

(75) Inventors: Stephen Van Dien, Kawasaki (JP); Shintaro Iwatani, Kawasaki (JP); Yoshihiro Usuda, Kawasaki (JP); Kazuhiko Matsui, Kawasaki (JP); Yuta Nakai, Kawasaki (JP); Tomoko Suzuki, Kawasaki (JP); Mika Moriya, Kawasaki (JP); Yuichiro Tsuji, Kawasaki (JP); Takuji Ueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/275,437

(22) Filed: Jan. 3, 2006

(65) Prior Publication Data

US 2006/0154344 A1 Jul. 13, 2006

Related U.S. Application Data

(63) Continuation of application No. PCT/JP2004/011220, filed on Jul. 29, 2004.

(30) Foreign Application Priority Data

Jul. 29, 2003 (JP) ............................. 2003-202842

(51) Int. Cl.
 *C12P 13/08* (2006.01)
 *C12N 9/04* (2006.01)
 *C12N 1/21* (2006.01)
 *C07H 21/04* (2006.01)

(52) U.S. Cl. .................. 435/115; 435/190; 435/252.33; 536/23.2

(58) Field of Classification Search ................ None
See application file for complete search history.

(56) References Cited

U.S. PATENT DOCUMENTS

| | | | |
|---|---|---|---|
| 5,175,107 | A | 12/1992 | Debabov et al. |
| 6,132,999 | A | 10/2000 | Debabov et al. |
| 6,297,031 | B1 | 10/2001 | Debabov et al. |
| 6,830,903 | B1 | 12/2004 | O'Donohue et al. |
| 6,911,332 | B2 | 6/2005 | Usuda et al. |
| 2002/0155556 | A1 | 10/2002 | Imaizumi et al. |
| 2002/0160461 | A1 | 10/2002 | Nakai et al. |
| 2003/0077764 | A1 | 4/2003 | Tsujimoto et al. |
| 2003/0138918 | A1 | 7/2003 | Iwatani et al. |
| 2004/0009578 | A1 | 1/2004 | Bathe et al. |
| 2004/0121428 | A1 | 6/2004 | Sugimoto et al. |
| 2004/0170985 | A1 | 9/2004 | Usuda et al. |
| 2004/0170986 | A1 | 9/2004 | Usuda et al. |
| 2004/0170987 | A1 | 9/2004 | Usuda et al. |
| 2004/0180404 | A1 | 9/2004 | Ishikawa et al. |
| 2004/0229305 | A1 | 11/2004 | Usuda et al. |
| 2004/0265956 | A1 | 12/2004 | Takikawa et al. |
| 2005/0208634 | A1 | 9/2005 | Usuda et al. |
| 2005/0233308 | A1 | 10/2005 | Nishio et al. |
| 2006/0019355 | A1 | 1/2006 | Ueda et al. |
| 2006/0019356 | A1 | 1/2006 | Usuda et al. |
| 2006/0030010 | A1 | 2/2006 | Usuda et al. |
| 2006/0030011 | A1 | 2/2006 | Usuda et al. |
| 2006/0035347 | A1 | 2/2006 | Usuda et al. |

FOREIGN PATENT DOCUMENTS

| | | |
|---|---|---|
| EP | 1 217 076 | 6/2002 |
| FR | 2 796 080 | 1/2001 |

OTHER PUBLICATIONS

Hong, S. H., et al., "Importance of redox balance on the production of succinic acid by metabolically engineered *Escherichia coli*," Appl. Microbiol. Biotechnol. 2002;58:286-290.
Iwakura, M., et al., "Studies on Regulatory Function of Malic Enzymes. VI. Purification and Molecular Properties of NADP-linked Malic Enzyme from *Escherichia coli* $W^1$," J. Biochem. 1979;85:1355-1365.
Kegg Genes b1479, 2 pp., www.genome.ad.jp/dbget-bin/www_bget?eco:b1479.
Kegg Genes b2463, 2 pp., www.genome.ad.jp/dbget-bin/www_bget?eco:b2463.
Mahajan, S. K., et al., "Physical Analysis of Spontaneous and Mutagen-Induced Mutants of *Escherichia coli* K-12 Expressing DNA Exonuclease VIII Activity," Genetics 1990;125:261-273.
Stols, L., et al., "Production of Succinic Acid through Overexpression of $NAD^+$-Dependent Malic Enzyme in an *Escherichia coli* Mutant," Appl. Environmen. Microbiol. 1997;63(7):2695-2701.
Emmerling, M., et al., "Metabolic Flux Responses to Pyruvate Kinase Knockout in *Escherichia coli*," J. Bacteriol. 2002;184(1):152-164.
Oh, M-K., et al., "Global Expression Profiling of Acetate-grown *Escherichia coli*," J. Biol. Chem. 2002;277(15):13175-13183.
Van Der Rest, M. E., et al., "Functions of the Membrane-Associated and Cytoplasmic Malate Dehydrogenases in the Citric Acid Cycle of *Escherichia coli*," J. Bacteriol. 2000;182(24):6892-6899.
International Search Report for PCT App. No. PCT/JP2004/011220 (Nov. 17, 2004).
Written Opinion for PCT App. No. PCT/JP2004/01120 (Feb. 17, 2006).
U.S. Appl. No. 09/868,338, filed Jun. 18, 2001, Kanno et al.
U.S. Appl. No. 10/149,450, filed Jun. 27, 2002, Nakanishi et al.
U.S. Appl. No. 60/644,040, filed Jan. 18, 2005, Kataoka et al.
U.S. Appl. No. 60/673,338, filed Apr. 21, 2005, Kataoka et al.
U.S. Appl. No. 60/695,846, filed Jul. 5, 2005, Tsuji et al.

(Continued)

*Primary Examiner*—Elizabeth Slobodyansky
(74) *Attorney, Agent, or Firm*—Shelly Guest Cermak; Cermak Kenealy & Vaidya LLP

(57) ABSTRACT

A bacterium belonging to the genus *Escherichia* which has an ability to produce L-lysine or L-threonine and which is modified so that a malic enzyme does not function normally in a cell, and a method for producing L-lysine or L-threonine, comprising culturing the bacterium in a medium to produce and cause accumulation of L-lysine or L-threonine, and collecting the L-lysine or L-threonine from the medium.

11 Claims, 4 Drawing Sheets

OTHER PUBLICATIONS

U.S. Appl. No. 11/199,387, filed Aug. 9, 2005, Usuda et al.
U.S. Appl. No. 11/247,138, filed Oct. 12, 2005, Rybak et al.
U.S. Appl. No. 11/275,562, filed Jan. 17, 2006, Kataoka et al.
U.S. Appl. No. 11/275,900, filed Feb. 2, 2006, Tsujimoto et al.
Office Action from European Patent App. No. 04771247.6 (Jul. 31, 2007).
Office Action from European Patent App. No. 04771247.6 (Jul. 31, 2007).

SEQUENCE LISTING

<160> NUMBER OF SEQ ID NOS: 41

<210> SEQ ID NO 1
<211> LENGTH: 54
<212> TYPE: DNA
<213> ORGANISM: Artificial Sequence
<220> FEATURE:
<223> OTHER INFORMATION: primer

<400> SEQUENCE: 1
aatatctttc agttccggca gtaccatacc ttcgcctgaa gcctgctttt ttat        54

<210> SEQ ID NO 2
<211> LENGTH: 54
<212> TYPE: DNA
<213> ORGANISM: Artificial Sequence
<220> FEATURE:
<223> OTHER INFORMATION: primer

<400> SEQUENCE: 2
agcatggaag aacgccgtaa cttcaacctg ctgggcgct caagttagta taaa          54

<210> SEQ ID NO 3
<211> LENGTH: 54
<212> TYPE: DNA
<213> ORGANISM: Artificial Sequence
<220> FEATURE:
<223> OTHER INFORMATION: primer

<400> SEQUENCE: 3
cgacgggcag tcagaagaac caaagttgga gtgcgatgaa gcctgctttt ttat        54

<210> SEQ ID NO 4
<211> LENGTH: 54
<212> TYPE: DNA
<213> ORGANISM: Artificial Sequence
<220> FEATURE:
<223> OTHER INFORMATION: primer

```
<400> SEQUENCE: 4
gacattgaag ttgacgaact cgacccggac aaatttcgct caagttagta taaa        54

<210> SEQ ID NO 5
<211> LENGTH: 1725
<212> TYPE: DNA
<213> ORGANISM: Escherichia coli
<220> FEATURE:
<221> NAME/KEY: CDS
<222> LOCATION: (1)..(1725)

<400> SEQUENCE: 5 atg gat att caa aaa aga gtg agt gac atg gaa cca aaa aca aaa aaa        48
Met Asp Ile Gln Lys Arg Val Ser Asp Met Glu Pro Lys Thr Lys Lys
1               5                   10                  15 cag cgt tcg ctt tat atc cct tac gct ggc cct gta ctg ctg gaa ttt        96
Gln Arg Ser Leu Tyr Ile Pro Tyr Ala Gly Pro Val Leu Leu Glu Phe
            20                  25                  30 ccg ttg ttg aat aaa ggc agt gcc ttc agc atg gaa gaa cgc cgt aac       144
Pro Leu Leu Asn Lys Gly Ser Ala Phe Ser Met Glu Glu Arg Arg Asn
        35                  40                  45 ttc aac ctg ctg ggg tta ctg ccg gaa gtg gtc gaa acc atc gaa gaa       192
Phe Asn Leu Leu Gly Leu Leu Pro Glu Val Val Glu Thr Ile Glu Glu
    50                  55                  60 caa gcg gaa cga gca tgg atc cag tat cag gga ttc aaa acc gaa atc       240
Gln Ala Glu Arg Ala Trp Ile Gln Tyr Gln Gly Phe Lys Thr Glu Ile
65                  70                  75                  80 gac aaa cac atc tac ctg cgt aac atc cag gac act aac gaa acc ctc       288
Asp Lys His Ile Tyr Leu Arg Asn Ile Gln Asp Thr Asn Glu Thr Leu
                85                  90                  95 ttc tac cgt ctg gta aac aat cat ctt gat gag atg atg cct gtt att       336
Phe Tyr Arg Leu Val Asn Asn His Leu Asp Glu Met Met Pro Val Ile
            100                 105                 110 tat acc cca acc gtc ggc gca gcc tgt gag cgt ttt tct gag atc tac       384
Tyr Thr Pro Thr Val Gly Ala Ala Cys Glu Arg Phe Ser Glu Ile Tyr
        115                 120                 125 cgc cgt tca cgc ggc gtg ttt atc tct tac cag aac cgg cac aat atg       432
Arg Arg Ser Arg Gly Val Phe Ile Ser Tyr Gln Asn Arg His Asn Met
    130                 135                 140 gac gat att ctg caa aac gtg ccg aac cat aat att aaa gtg att gtg       480
Asp Asp Ile Leu Gln Asn Val Pro Asn His Asn Ile Lys Val Ile Val
145                 150                 155                 160 gtg act gac ggt gaa cgc att ctg ggg ctt ggt gac cag ggc atc ggc       528
Val Thr Asp Gly Glu Arg Ile Leu Gly Leu Gly Asp Gln Gly Ile Gly
                165                 170                 175 ggg atg ggc att ccg atc ggt aaa ctg tcg ctc tat acc gcc tgt ggc       576
Gly Met Gly Ile Pro Ile Gly Lys Leu Ser Leu Tyr Thr Ala Cys Gly
            180                 185                 190 ggc atc agc ccg gcg tat acc ctt ccg gtg gtg ctg gat gtc gga acg       624
Gly Ile Ser Pro Ala Tyr Thr Leu Pro Val Val Leu Asp Val Gly Thr
        195                 200                 205 aac aac caa cag ctg ctt aac gat ccg ctg tat atg ggc tgg cgt aat       672
Asn Asn Gln Gln Leu Leu Asn Asp Pro Leu Tyr Met Gly Trp Arg Asn
    210                 215                 220 ccg cgt atc act gac gac gaa tac tat gaa ttc gtt gat gaa ttt atc       720
Pro Arg Ile Thr Asp Asp Glu Tyr Tyr Glu Phe Val Asp Glu Phe Ile
225                 230                 235                 240 cag gct gtg aaa caa cgc tgg cca gac gtg ctg ttg cag ttt gaa gac       768
Gln Ala Val Lys Gln Arg Trp Pro Asp Val Leu Leu Gln Phe Glu Asp
                245                 250                 255
```

```
                                        -continued ttt gct caa aaa aat gcg atg ccg tta ctt aac cgc tat cgc aat gaa    816
Phe Ala Gln Lys Asn Ala Met Pro Leu Leu Asn Arg Tyr Arg Asn Glu
            260                 265                 270 att tgt tct ttt aac gat gac att cag ggc act gcg gcg gta aca gtc    864
Ile Cys Ser Phe Asn Asp Asp Ile Gln Gly Thr Ala Ala Val Thr Val
        275                 280                 285 ggc aca ctg atc gca gca agc cgc gcg gca ggt ggt cag tta agc gag    912
Gly Thr Leu Ile Ala Ala Ser Arg Ala Ala Gly Gly Gln Leu Ser Glu
    290                 295                 300 aaa aaa atc gtc ttc ctt ggc gca ggt tca gcg gga tgc ggc att gcc    960
Lys Lys Ile Val Phe Leu Gly Ala Gly Ser Ala Gly Cys Gly Ile Ala
305                 310                 315                 320 gaa atg atc atc tcc cag acc cag cgc gaa gga tta agc gag gaa gcg   1008
Glu Met Ile Ile Ser Gln Thr Gln Arg Glu Gly Leu Ser Glu Glu Ala
                325                 330                 335 gcg cgg cag aaa gtc ttt atg gtc gat cgc ttt ggc ttg ctg act gac   1056
Ala Arg Gln Lys Val Phe Met Val Asp Arg Phe Gly Leu Leu Thr Asp
            340                 345                 350 aag atg ccg aac ctg ctg cct ttc cag acc aaa ctg gtg cag aag cgc   1104
Lys Met Pro Asn Leu Leu Pro Phe Gln Thr Lys Leu Val Gln Lys Arg
        355                 360                 365 gaa aac ctc agt gac tgg gat acc gac agc gat gtg ctg tca ctg ctg   1152
Glu Asn Leu Ser Asp Trp Asp Thr Asp Ser Asp Val Leu Ser Leu Leu
    370                 375                 380 gat gtg gtg cgc aat gta aaa cca gat att ctg att ggc gtc tca gga   1200
Asp Val Val Arg Asn Val Lys Pro Asp Ile Leu Ile Gly Val Ser Gly
385                 390                 395                 400 cag acc ggg ctg ttt acg gaa gag atc atc cgt gag atg cat aaa cac   1248
Gln Thr Gly Leu Phe Thr Glu Glu Ile Ile Arg Glu Met His Lys His
                405                 410                 415 tgt ccg cgt ccg atc gtg atg ccg ctg tct aac ccg acg tca cgc gtg   1296
Cys Pro Arg Pro Ile Val Met Pro Leu Ser Asn Pro Thr Ser Arg Val
            420                 425                 430 gaa gcc aca ccg cag gac att atc gcc tgg acc gaa ggt aac gcg ctg   1344
Glu Ala Thr Pro Gln Asp Ile Ile Ala Trp Thr Glu Gly Asn Ala Leu
        435                 440                 445 gtc gcc acg ggc agc ccg ttt aat cca gtg gta tgg aaa gat aaa atc   1392
Val Ala Thr Gly Ser Pro Phe Asn Pro Val Val Trp Lys Asp Lys Ile
    450                 455                 460 tac cct atc gcc cag tgt aac aac gcc ttt att ttc ccg ggc atc ggc   1440
Tyr Pro Ile Ala Gln Cys Asn Asn Ala Phe Ile Phe Pro Gly Ile Gly
465                 470                 475                 480 ctg ggt gtt att gct tcc ggc gcg tca cgt atc acc gat gag atg ctg   1488
Leu Gly Val Ile Ala Ser Gly Ala Ser Arg Ile Thr Asp Glu Met Leu
                485                 490                 495 atg tcg gca agt gaa acg ctg gcg cag tat tca cca ttg gtg ctg aac   1536
Met Ser Ala Ser Glu Thr Leu Ala Gln Tyr Ser Pro Leu Val Leu Asn
            500                 505                 510 ggc gaa ggt atg gta ctg ccg gaa ctg aaa gat att cag aaa gtc tcc   1584
Gly Glu Gly Met Val Leu Pro Glu Leu Lys Asp Ile Gln Lys Val Ser
        515                 520                 525 cgc gca att gcg ttt gcg gtt ggc aaa atg gcg cag cag caa ggc gtg   1632
Arg Ala Ile Ala Phe Ala Val Gly Lys Met Ala Gln Gln Gln Gly Val
    530                 535                 540 gcg gtg aaa acc tct gcc gaa gcc ctg caa cag gcc att gac gat aat   1680
Ala Val Lys Thr Ser Ala Glu Ala Leu Gln Gln Ala Ile Asp Asp Asn
545                 550                 555                 560 ttc tgg caa gcc gaa tac cgc gac tac cgc cgt acc tcc atc taa      1725
Phe Trp Gln Ala Glu Tyr Arg Asp Tyr Arg Arg Thr Ser Ile
                565                 570
```

<210> SEQ ID NO 6
<211> LENGTH: 574
<212> TYPE: PRT
<213> ORGANISM: Escherichia coli

<400> SEQUENCE: 6

```
Met Asp Ile Gln Lys Arg Val Ser Asp Met Glu Pro Lys Thr Lys Lys
1               5                   10                  15

Gln Arg Ser Leu Tyr Ile Pro Tyr Ala Gly Pro Val Leu Leu Glu Phe
            20                  25                  30

Pro Leu Leu Asn Lys Gly Ser Ala Phe Ser Met Glu Glu Arg Arg Asn
        35                  40                  45

Phe Asn Leu Leu Gly Leu Leu Pro Glu Val Val Glu Thr Ile Glu Glu
50                  55                  60

Gln Ala Glu Arg Ala Trp Ile Gln Tyr Gln Gly Phe Lys Thr Glu Ile
65                  70                  75                  80

Asp Lys His Ile Tyr Leu Arg Asn Ile Gln Asp Thr Asn Glu Thr Leu
                85                  90                  95

Phe Tyr Arg Leu Val Asn Asn His Leu Asp Glu Met Met Pro Val Ile
            100                 105                 110

Tyr Thr Pro Thr Val Gly Ala Ala Cys Glu Arg Phe Ser Glu Ile Tyr
        115                 120                 125

Arg Arg Ser Arg Gly Val Phe Ile Ser Tyr Gln Asn Arg His Asn Met
130                 135                 140

Asp Asp Ile Leu Gln Asn Val Pro Asn His Asn Ile Lys Val Ile Val
145                 150                 155                 160

Val Thr Asp Gly Glu Arg Ile Leu Gly Leu Gly Asp Gln Gly Ile Gly
                165                 170                 175

Gly Met Gly Ile Pro Ile Gly Lys Leu Ser Leu Tyr Thr Ala Cys Gly
            180                 185                 190

Gly Ile Ser Pro Ala Tyr Thr Leu Pro Val Val Leu Asp Val Gly Thr
        195                 200                 205

Asn Asn Gln Gln Leu Leu Asn Asp Pro Leu Tyr Met Gly Trp Arg Asn
210                 215                 220

Pro Arg Ile Thr Asp Asp Glu Tyr Tyr Glu Phe Val Asp Glu Phe Ile
225                 230                 235                 240

Gln Ala Val Lys Gln Arg Trp Pro Asp Val Leu Leu Gln Phe Glu Asp
                245                 250                 255

Phe Ala Gln Lys Asn Ala Met Pro Leu Leu Asn Arg Tyr Arg Asn Glu
            260                 265                 270

Ile Cys Ser Phe Asn Asp Asp Ile Gln Gly Thr Ala Ala Val Thr Val
        275                 280                 285

Gly Thr Leu Ile Ala Ala Ser Arg Ala Ala Gly Gly Gln Leu Ser Glu
290                 295                 300

Lys Lys Ile Val Phe Leu Gly Ala Gly Ser Ala Gly Cys Gly Ile Ala
305                 310                 315                 320

Glu Met Ile Ile Ser Gln Thr Gln Arg Glu Gly Leu Ser Glu Glu Ala
                325                 330                 335

Ala Arg Gln Lys Val Phe Met Val Asp Arg Phe Gly Leu Leu Thr Asp
            340                 345                 350

Lys Met Pro Asn Leu Leu Pro Phe Gln Thr Lys Leu Val Gln Lys Arg
        355                 360                 365

Glu Asn Leu Ser Asp Trp Asp Thr Asp Ser Asp Val Leu Ser Leu Leu
```

```
                  370                 375                 380
Asp Val Val Arg Asn Val Lys Pro Asp Ile Leu Ile Gly Val Ser Gly
385                 390                 395                 400

Gln Thr Gly Leu Phe Thr Glu Glu Ile Ile Arg Glu Met His Lys His
                405                 410                 415

Cys Pro Arg Pro Ile Val Met Pro Leu Ser Asn Pro Thr Ser Arg Val
            420                 425                 430

Glu Ala Thr Pro Gln Asp Ile Ile Ala Trp Thr Gly Asn Ala Leu
        435                 440                 445

Val Ala Thr Gly Ser Pro Phe Asn Pro Val Val Trp Lys Asp Lys Ile
450                 455                 460

Tyr Pro Ile Ala Gln Cys Asn Asn Ala Phe Ile Phe Pro Gly Ile Gly
465                 470                 475                 480

Leu Gly Val Ile Ala Ser Gly Ala Ser Arg Ile Thr Asp Glu Met Leu
                485                 490                 495

Met Ser Ala Ser Glu Thr Leu Ala Gln Tyr Ser Pro Leu Val Leu Asn
            500                 505                 510

Gly Glu Gly Met Val Leu Pro Glu Leu Lys Asp Ile Gln Lys Val Ser
        515                 520                 525

Arg Ala Ile Ala Phe Ala Val Gly Lys Met Ala Gln Gln Gly Val
        530                 535                 540

Ala Val Lys Thr Ser Ala Glu Ala Leu Gln Gln Ala Ile Asp Asp Asn
545                 550                 555                 560

Phe Trp Gln Ala Glu Tyr Arg Asp Tyr Arg Arg Thr Ser Ile
                565                 570

<210> SEQ ID NO 7
<211> LENGTH: 2280
<212> TYPE: DNA
<213> ORGANISM: Escherichia coli
<220> FEATURE:
<221> NAME/KEY: CDS
<222> LOCATION: (1)..(2280)

<400> SEQUENCE: 7 atg gat gac cag tta aaa caa agt gca ctt gat ttc cat gaa ttt cca        48
Met Asp Asp Gln Leu Lys Gln Ser Ala Leu Asp Phe His Glu Phe Pro
1               5                  10                  15 gtt cca ggg aaa atc cag gtt tct cca acc aag cct ctg gca aca cag        96
Val Pro Gly Lys Ile Gln Val Ser Pro Thr Lys Pro Leu Ala Thr Gln
            20                  25                  30 cgc gat ctg gcg ctg gcc tac tca cca ggc gtt gcc gca cct tgt ctt       144
Arg Asp Leu Ala Leu Ala Tyr Ser Pro Gly Val Ala Ala Pro Cys Leu
        35                  40                  45 gaa atc gaa aaa gac ccg tta aaa gcc tac aaa tat acc gcc cga ggt       192
Glu Ile Glu Lys Asp Pro Leu Lys Ala Tyr Lys Tyr Thr Ala Arg Gly
    50                  55                  60 aac ctg gtg gcg gtg atc tct aac ggt acg gcg gtg ctg ggg tta ggc       240
Asn Leu Val Ala Val Ile Ser Asn Gly Thr Ala Val Leu Gly Leu Gly
65                  70                  75                  80 aac att ggc gcg ctg gca ggc aaa ccg gtg atg gaa ggc aag ggc gtt       288
Asn Ile Gly Ala Leu Ala Gly Lys Pro Val Met Glu Gly Lys Gly Val
                85                  90                  95 ctg ttt aag aaa ttc gcc ggg att gat gta ttt gac att gaa gtt gac       336
Leu Phe Lys Lys Phe Ala Gly Ile Asp Val Phe Asp Ile Glu Val Asp
            100                 105                 110 gaa ctc gac ccg gac aaa ttt att gaa gtt gtc gcc gcg ctc gaa cca       384
Glu Leu Asp Pro Asp Lys Phe Ile Glu Val Val Ala Ala Leu Glu Pro
```

```
                    115                 120                 125
acc ttc ggc ggc atc aac ctc gaa gac att aaa gcg cca gaa tgt ttc    432
Thr Phe Gly Gly Ile Asn Leu Glu Asp Ile Lys Ala Pro Glu Cys Phe
    130                 135                 140 tat att gaa cag aaa ctg cgc gag cgg atg aat att ccg gta ttc cac    480
Tyr Ile Glu Gln Lys Leu Arg Glu Arg Met Asn Ile Pro Val Phe His
145                 150                 155                 160 gac gat cag cac ggc acg gca att atc agc act gcc gcc atc ctc aac    528
Asp Asp Gln His Gly Thr Ala Ile Ile Ser Thr Ala Ala Ile Leu Asn
                165                 170                 175 ggc ttg cgc gtg gtg gag aaa aac atc tcc gac gtg cgg atg gtg gtt    576
Gly Leu Arg Val Val Glu Lys Asn Ile Ser Asp Val Arg Met Val Val
            180                 185                 190 tcc ggc gcg ggt gcc gca gca atc gcc tgt atg aac ctg ctg gta gcg    624
Ser Gly Ala Gly Ala Ala Ala Ile Ala Cys Met Asn Leu Leu Val Ala
        195                 200                 205 ctg ggt ctg caa aaa cat aac atc gtg gtt tgc gat tca aaa ggc gtt    672
Leu Gly Leu Gln Lys His Asn Ile Val Val Cys Asp Ser Lys Gly Val
    210                 215                 220 atc tat cag ggc cgt gag cca aac atg gcg gaa acc aaa gcc gca tat    720
Ile Tyr Gln Gly Arg Glu Pro Asn Met Ala Glu Thr Lys Ala Ala Tyr
225                 230                 235                 240 gcg gtg gtg gat gac ggc aaa cgt acc ctc gat gat gtg att gaa ggc    768
Ala Val Val Asp Asp Gly Lys Arg Thr Leu Asp Asp Val Ile Glu Gly
                245                 250                 255 gcg gat att ttc ctg ggc tgt tcc ggc ccg aaa gtg ctg acc cag gaa    816
Ala Asp Ile Phe Leu Gly Cys Ser Gly Pro Lys Val Leu Thr Gln Glu
            260                 265                 270 atg gtg aag aaa atg gct cgt gcg cca atg atc ctg gcg ctg gcg aac    864
Met Val Lys Lys Met Ala Arg Ala Pro Met Ile Leu Ala Leu Ala Asn
        275                 280                 285 ccg gaa ccg gaa att ctg ccg ccg ctg gcg aaa gaa gtg cgt ccg gat    912
Pro Glu Pro Glu Ile Leu Pro Pro Leu Ala Lys Glu Val Arg Pro Asp
    290                 295                 300 gcc atc att tgc acc ggt cgt tct gac tat ccg aac cag gtg aac aac    960
Ala Ile Ile Cys Thr Gly Arg Ser Asp Tyr Pro Asn Gln Val Asn Asn
305                 310                 315                 320 gtc ctg tgc ttc ccg ttc atc ttc cgt ggc gcg ctg gac gtt ggc gca   1008
Val Leu Cys Phe Pro Phe Ile Phe Arg Gly Ala Leu Asp Val Gly Ala
                325                 330                 335 acc gcc atc aac gaa gag atg aaa ctg gcg gcg gta cgt gcg att gca   1056
Thr Ala Ile Asn Glu Glu Met Lys Leu Ala Ala Val Arg Ala Ile Ala
            340                 345                 350 gaa ctc gcc cat gcg gaa cag agc gaa gtg gtg gct tca gcg tat ggc   1104
Glu Leu Ala His Ala Glu Gln Ser Glu Val Val Ala Ser Ala Tyr Gly
        355                 360                 365 gat cag gat ctg agc ttt ggt ccg gaa tac atc att cca aaa ccg ttt   1152
Asp Gln Asp Leu Ser Phe Gly Pro Glu Tyr Ile Ile Pro Lys Pro Phe
    370                 375                 380 gat ccg cgc ttg atc gtt aag atc gct cct gcg gtc gct aaa gcc gcg   1200
Asp Pro Arg Leu Ile Val Lys Ile Ala Pro Ala Val Ala Lys Ala Ala
385                 390                 395                 400 atg gag tcg ggc gtg gcg act cgt ccg att gct gat ttc gac gtc tac   1248
Met Glu Ser Gly Val Ala Thr Arg Pro Ile Ala Asp Phe Asp Val Tyr
                405                 410                 415 atc gac aag ctg act gag ttc gtt tac aaa acc aac ctg ttt atg aag   1296
Ile Asp Lys Leu Thr Glu Phe Val Tyr Lys Thr Asn Leu Phe Met Lys
            420                 425                 430 ccg att ttc tcc cag gct cgc aaa gcg ccg aag cgc gtt gtt ctg ccg   1344
```

-continued

```
                    Pro Ile Phe Ser Gln Ala Arg Lys Ala Pro Lys Arg Val Val Leu Pro
                            435                 440                 445 gaa ggg gaa gag gcg cgc gtt ctg cat gcc act cag gaa ctg gta acg        1392
Glu Gly Glu Glu Ala Arg Val Leu His Ala Thr Gln Glu Leu Val Thr
450                 455                 460 ctg gga ctg gcg aaa ccg atc ctt atc ggt cgt ccg aac gtg atc gaa        1440
Leu Gly Leu Ala Lys Pro Ile Leu Ile Gly Arg Pro Asn Val Ile Glu
465                 470                 475                 480 atg cgc att cag aaa ctg ggc ttg cag atc aaa gcg ggc gtt gat ttt        1488
Met Arg Ile Gln Lys Leu Gly Leu Gln Ile Lys Ala Gly Val Asp Phe
            485                 490                 495 gag atc gtc aat aac gaa tcc gat ccg cgc ttt aaa gag tac tgg acc        1536
Glu Ile Val Asn Asn Glu Ser Asp Pro Arg Phe Lys Glu Tyr Trp Thr
        500                 505                 510 gaa tac ttc cag atc atg aag cgt cgc ggc gtc act cag gaa cag gcg        1584
Glu Tyr Phe Gln Ile Met Lys Arg Arg Gly Val Thr Gln Glu Gln Ala
    515                 520                 525 cag cgg gcg ctg atc agt aac ccg aca gtg atc ggc gcg atc atg gtt        1632
Gln Arg Ala Leu Ile Ser Asn Pro Thr Val Ile Gly Ala Ile Met Val
530                 535                 540 cag cgt ggg gaa gcc gat gca atg att tgc ggt acg gtg ggt gat tat        1680
Gln Arg Gly Glu Ala Asp Ala Met Ile Cys Gly Thr Val Gly Asp Tyr
545                 550                 555                 560 cat gaa cat ttt agc gtg gtg aaa aat gtc ttt ggt tat cgc gat ggc        1728
His Glu His Phe Ser Val Val Lys Asn Val Phe Gly Tyr Arg Asp Gly
            565                 570                 575 gtt cac acc gca ggt gcc atg aac gcg ctg ctg ctg ccg agt ggt aac        1776
Val His Thr Ala Gly Ala Met Asn Ala Leu Leu Leu Pro Ser Gly Asn
        580                 585                 590 acc ttt att gcc gat aca tat gtt aat gat gaa ccg gat gca gaa gag        1824
Thr Phe Ile Ala Asp Thr Tyr Val Asn Asp Glu Pro Asp Ala Glu Glu
    595                 600                 605 ctg gcg gag atc acc ttg atg gcg gca gaa act gtc cgt cgt ttt ggt        1872
Leu Ala Glu Ile Thr Leu Met Ala Ala Glu Thr Val Arg Arg Phe Gly
610                 615                 620 att gag ccg cgc gtt gct ttg ttg tcg cac tcc aac ttt ggt tct tct        1920
Ile Glu Pro Arg Val Ala Leu Leu Ser His Ser Asn Phe Gly Ser Ser
625                 630                 635                 640 gac tgc ccg tcg tcg agc aaa atg cgt cag gcg ctg gaa ctg gtc agg        1968
Asp Cys Pro Ser Ser Ser Lys Met Arg Gln Ala Leu Glu Leu Val Arg
            645                 650                 655 gaa cgt gca cca gaa ctg atg att gat ggt gaa atg cac ggc gat gca        2016
Glu Arg Ala Pro Glu Leu Met Ile Asp Gly Glu Met His Gly Asp Ala
        660                 665                 670 gcg ctg gtg gaa gcg att cgc aac gac cgt atg ccg gac agc tct ttg        2064
Ala Leu Val Glu Ala Ile Arg Asn Asp Arg Met Pro Asp Ser Ser Leu
    675                 680                 685 aaa ggt tcc gcc aat att ctg gtg atg ccg aac atg gaa gct gcc cgc        2112
Lys Gly Ser Ala Asn Ile Leu Val Met Pro Asn Met Glu Ala Ala Arg
690                 695                 700 att agt tac aac tta ctg cgt gtt tcc agc tcg gaa ggt gtg act gtc        2160
Ile Ser Tyr Asn Leu Leu Arg Val Ser Ser Ser Glu Gly Val Thr Val
705                 710                 715                 720 ggc ccg gtg ctg atg ggt gtg gcg aaa ccg gtt cac gtg tta acg ccg        2208
Gly Pro Val Leu Met Gly Val Ala Lys Pro Val His Val Leu Thr Pro
            725                 730                 735 atc gca tcg gtg cgt cgt atc gtc aac atg gtg gcg ctg gcc gtg gta        2256
Ile Ala Ser Val Arg Arg Ile Val Asn Met Val Ala Leu Ala Val Val
        740                 745                 750
```

```
                                      -continued
gaa gcg caa acc caa ccg ctg taa                                          2280
Glu Ala Gln Thr Gln Pro Leu
        755
```

<210> SEQ ID NO 8
<211> LENGTH: 759
<212> TYPE: PRT
<213> ORGANISM: Escherichia coli

<400> SEQUENCE: 8

```
Met Asp Asp Gln Leu Lys Gln Ser Ala Leu Asp Phe His Glu Phe Pro
1               5                   10                  15

Val Pro Gly Lys Ile Gln Val Ser Pro Thr Lys Pro Leu Ala Thr Gln
            20                  25                  30

Arg Asp Leu Ala Leu Ala Tyr Ser Pro Gly Val Ala Ala Pro Cys Leu
        35                  40                  45

Glu Ile Glu Lys Asp Pro Leu Lys Ala Tyr Lys Tyr Thr Ala Arg Gly
    50                  55                  60

Asn Leu Val Ala Val Ile Ser Asn Gly Thr Ala Val Leu Gly Leu Gly
65                  70                  75                  80

Asn Ile Gly Ala Leu Ala Gly Lys Pro Val Met Glu Gly Lys Gly Val
                85                  90                  95

Leu Phe Lys Lys Phe Ala Gly Ile Asp Val Phe Asp Ile Glu Val Asp
            100                 105                 110

Glu Leu Asp Pro Asp Lys Phe Ile Glu Val Val Ala Ala Leu Glu Pro
        115                 120                 125

Thr Phe Gly Gly Ile Asn Leu Glu Asp Ile Lys Ala Pro Glu Cys Phe
    130                 135                 140

Tyr Ile Glu Gln Lys Leu Arg Glu Arg Met Asn Ile Pro Val Phe His
145                 150                 155                 160

Asp Asp Gln His Gly Thr Ala Ile Ile Ser Thr Ala Ala Ile Leu Asn
                165                 170                 175

Gly Leu Arg Val Val Glu Lys Asn Ile Ser Asp Val Arg Met Val Val
            180                 185                 190

Ser Gly Ala Gly Ala Ala Ala Ile Ala Cys Met Asn Leu Leu Val Ala
        195                 200                 205

Leu Gly Leu Gln Lys His Asn Ile Val Val Cys Asp Ser Lys Gly Val
    210                 215                 220

Ile Tyr Gln Gly Arg Glu Pro Asn Met Ala Glu Thr Lys Ala Ala Tyr
225                 230                 235                 240

Ala Val Val Asp Asp Gly Lys Arg Thr Leu Asp Val Ile Glu Gly
                245                 250                 255

Ala Asp Ile Phe Leu Gly Cys Ser Gly Pro Lys Val Leu Thr Gln Glu
            260                 265                 270

Met Val Lys Lys Met Ala Arg Ala Pro Met Ile Leu Ala Leu Ala Asn
        275                 280                 285

Pro Glu Pro Glu Ile Leu Pro Pro Leu Ala Lys Glu Val Arg Pro Asp
    290                 295                 300

Ala Ile Ile Cys Thr Gly Arg Ser Asp Tyr Pro Asn Gln Val Asn Asn
305                 310                 315                 320

Val Leu Cys Phe Pro Phe Ile Phe Arg Gly Ala Leu Asp Val Gly Ala
                325                 330                 335

Thr Ala Ile Asn Glu Glu Met Lys Leu Ala Ala Val Arg Ala Ile Ala
            340                 345                 350

Glu Leu Ala His Ala Glu Gln Ser Glu Val Val Ala Ser Ala Tyr Gly
```

```
                355                 360                 365
Asp Gln Asp Leu Ser Phe Gly Pro Glu Tyr Ile Ile Pro Lys Pro Phe
        370                 375                 380

Asp Pro Arg Leu Ile Val Lys Ile Ala Pro Val Ala Lys Ala Ala
385                 390                 395                 400

Met Glu Ser Gly Val Ala Thr Arg Pro Ile Ala Asp Phe Asp Val Tyr
                405                 410                 415

Ile Asp Lys Leu Thr Glu Phe Val Tyr Lys Thr Asn Leu Phe Met Lys
        420                 425                 430

Pro Ile Phe Ser Gln Ala Arg Lys Ala Pro Lys Arg Val Val Leu Pro
        435                 440                 445

Glu Gly Glu Ala Arg Val Leu His Ala Thr Gln Glu Leu Val Thr
450                 455                 460

Leu Gly Leu Ala Lys Pro Ile Leu Ile Gly Arg Pro Asn Val Ile Glu
465                 470                 475                 480

Met Arg Ile Gln Lys Leu Gly Leu Gln Ile Lys Ala Gly Val Asp Phe
                485                 490                 495

Glu Ile Val Asn Asn Glu Ser Asp Pro Arg Phe Lys Glu Tyr Trp Thr
                500                 505                 510

Glu Tyr Phe Gln Ile Met Lys Arg Arg Gly Val Thr Gln Glu Gln Ala
        515                 520                 525

Gln Arg Ala Leu Ile Ser Asn Pro Thr Val Ile Gly Ala Ile Met Val
        530                 535                 540

Gln Arg Gly Glu Ala Asp Ala Met Ile Cys Gly Thr Val Gly Asp Tyr
545                 550                 555                 560

His Glu His Phe Ser Val Val Lys Asn Val Phe Gly Tyr Arg Asp Gly
                565                 570                 575

Val His Thr Ala Gly Ala Met Asn Ala Leu Leu Pro Ser Gly Asn
        580                 585                 590

Thr Phe Ile Ala Asp Thr Tyr Val Asn Asp Glu Pro Asp Ala Glu Glu
        595                 600                 605

Leu Ala Glu Ile Thr Leu Met Ala Ala Glu Thr Val Arg Arg Phe Gly
610                 615                 620

Ile Glu Pro Arg Val Ala Leu Leu Ser His Ser Asn Phe Gly Ser Ser
625                 630                 635                 640

Asp Cys Pro Ser Ser Ser Lys Met Arg Gln Ala Leu Glu Leu Val Arg
                645                 650                 655

Glu Arg Ala Pro Glu Leu Met Ile Asp Gly Glu Met His Gly Asp Ala
                660                 665                 670

Ala Leu Val Glu Ala Ile Arg Asn Asp Arg Met Pro Asp Ser Ser Leu
        675                 680                 685

Lys Gly Ser Ala Asn Ile Leu Val Met Pro Asn Met Glu Ala Ala Arg
        690                 695                 700

Ile Ser Tyr Asn Leu Leu Arg Val Ser Ser Ser Glu Gly Val Thr Val
705                 710                 715                 720

Gly Pro Val Leu Met Gly Val Ala Lys Pro Val His Val Leu Thr Pro
                725                 730                 735

Ile Ala Ser Val Arg Arg Ile Val Asn Met Val Ala Leu Ala Val Val
                740                 745                 750

Glu Ala Gln Thr Gln Pro Leu
        755

<210> SEQ ID NO 9
```

-continued

```
<211> LENGTH: 101
<212> TYPE: DNA
<213> ORGANISM: lambda phage

<400> SEQUENCE: 9 cctgctttt tatactaagt tggcattata aaaaagcatt gcttatcaat ttgttgcaac      60
gaacaggtca ctatcagtca aaataaaatc attatttgat t                        101

<210> SEQ ID NO 10
<211> LENGTH: 172
<212> TYPE: DNA
<213> ORGANISM: lambda phage

<400> SEQUENCE: 10
gcgctaatgc tctgttacag gtcactaata ccatctaagt agttgattca tagtgactgc     60
atatgttgtg ttttacagta ttatgtagtc tgttttttat gcaaaatcta atttaatata   120
ttgatattta tcattttta cgtttctcgt tcagctttt tatactaact tg             172

<210> SEQ ID NO 11
<211> LENGTH: 120
<212> TYPE: DNA
<213> ORGANISM: lambda phage

<400> SEQUENCE: 11
agatcttgaa gcctgctttt ttatactaag ttggcattat aaaaaagcat tgcttatcaa    60
tttgttgcaa cgaacaggtc actatcagtc aaaataaaat cattatttga tttcgaattc   120

<210> SEQ ID NO 12
<211> LENGTH: 184
<212> TYPE: DNA
<213> ORGANISM: lambda phage

<400> SEQUENCE: 12
ctgcagtctg ttacaggtca ctaataccat ctaagtagtt gattcatagt gactgcatat    60
gttgtgtttt acagtattat gtagtctgtt ttttatgcaa aatctaattt aatatattga  120
tatttatatc attttacgtt tctcgttcag ctttttata ctaacttgag cgtctagaaa   180
gctt                                                                184

<210> SEQ ID NO 13
<211> LENGTH: 1071
<212> TYPE: DNA
<213> ORGANISM: lambda phage
<220> FEATURE:
<221> NAME/KEY: CDS
<222> LOCATION: (1)..(1071)

<400> SEQUENCE: 13 atg gga aga agg cga agt cat gag cgc cgg gat tta ccc cct aac ctt      48
Met Gly Arg Arg Arg Ser His Glu Arg Arg Asp Leu Pro Pro Asn Leu
1               5                   10                  15 tat ata aga aac aat gga tat tac tgc tac agg gac cca agg acg ggt      96
Tyr Ile Arg Asn Asn Gly Tyr Tyr Cys Tyr Arg Asp Pro Arg Thr Gly
            20                  25                  30 aaa gag ttt gga tta ggc aga gac agg cga atc gca atc act gaa gct    144
Lys Glu Phe Gly Leu Gly Arg Asp Arg Arg Ile Ala Ile Thr Glu Ala
        35                  40                  45 ata cag gcc aac att gag tta ttt tca gga cac aaa cac aag cct ctg    192
Ile Gln Ala Asn Ile Glu Leu Phe Ser Gly His Lys His Lys Pro Leu
    50                  55                  60
```

```
aca gcg aga atc aac agt gat aat tcc gtt acg tta cat tca tgg ctt      240
Thr Ala Arg Ile Asn Ser Asp Asn Ser Val Thr Leu His Ser Trp Leu
 65              70                  75                  80 gat cgc tac gaa aaa atc ctg gcc agc aga gga atc aag cag aag aca      288
Asp Arg Tyr Glu Lys Ile Leu Ala Ser Arg Gly Ile Lys Gln Lys Thr
                 85                  90                  95 ctc ata aat tac atg agc aaa att aaa gca ata agg agg ggt ctg cct      336
Leu Ile Asn Tyr Met Ser Lys Ile Lys Ala Ile Arg Arg Gly Leu Pro
                    100                 105                 110 gat gct cca ctt gaa gac atc acc aca aaa gaa att gcg gca atg ctc      384
Asp Ala Pro Leu Glu Asp Ile Thr Thr Lys Glu Ile Ala Ala Met Leu
                115                 120                 125 aat gga tac ata gac gag ggc aag gcg gcg tca gcc aag tta atc aga      432
Asn Gly Tyr Ile Asp Glu Gly Lys Ala Ala Ser Ala Lys Leu Ile Arg
130                 135                 140 tca acg ctg agc gat gca ttc cga gag gca ata gct gaa ggc cat ata      480
Ser Thr Leu Ser Asp Ala Phe Arg Glu Ala Ile Ala Glu Gly His Ile
145                 150                 155                 160 aca aca aac cat gtc gct gcc act cgc gca gca aaa tca gag gta agg      528
Thr Thr Asn His Val Ala Ala Thr Arg Ala Ala Lys Ser Glu Val Arg
                165                 170                 175 aga tca aga ctt acg gct gac gaa tac ctg aaa att tat caa gca gca      576
Arg Ser Arg Leu Thr Ala Asp Glu Tyr Leu Lys Ile Tyr Gln Ala Ala
                180                 185                 190 gaa tca tca cca tgt tgg ctc aga ctt gca atg gaa ctg gct gtt gtt      624
Glu Ser Ser Pro Cys Trp Leu Arg Leu Ala Met Glu Leu Ala Val Val
                195                 200                 205 acc ggg caa cga gtt ggt gat tta tgc gaa atg aag tgg tct gat atc      672
Thr Gly Gln Arg Val Gly Asp Leu Cys Glu Met Lys Trp Ser Asp Ile
210                 215                 220 gta gat gga tat ctt tat gtc gag caa agc aaa aca ggc gta aaa att      720
Val Asp Gly Tyr Leu Tyr Val Glu Gln Ser Lys Thr Gly Val Lys Ile
225                 230                 235                 240 gcc atc cca aca gca ttg cat att gat gct ctc gga ata tca atg aag      768
Ala Ile Pro Thr Ala Leu His Ile Asp Ala Leu Gly Ile Ser Met Lys
                245                 250                 255 gaa aca ctt gat aaa tgc aaa gag att ctt ggc gga gaa acc ata att      816
Glu Thr Leu Asp Lys Cys Lys Glu Ile Leu Gly Gly Glu Thr Ile Ile
                260                 265                 270 gca tct act cgt cgc gaa ccg ctt tca tcc ggc aca gta tca agg tat      864
Ala Ser Thr Arg Arg Glu Pro Leu Ser Ser Gly Thr Val Ser Arg Tyr
                275                 280                 285 ttt atg cgc gca cga aaa gca tca ggt ctt tcc ttc gaa ggg gat ccg      912
Phe Met Arg Ala Arg Lys Ala Ser Gly Leu Ser Phe Glu Gly Asp Pro
290                 295                 300 cct acc ttt cac gag ttg cgc agt ttg tct gca aga ctc tat gag aag      960
Pro Thr Phe His Glu Leu Arg Ser Leu Ser Ala Arg Leu Tyr Glu Lys
305                 310                 315                 320 cag ata agc gat aag ttt gct caa cat ctt ctc ggg cat aag tcg gac     1008
Gln Ile Ser Asp Lys Phe Ala Gln His Leu Leu Gly His Lys Ser Asp
                325                 330                 335 acc atg gca tca cag tat cgt gat gac aga ggc agg gag tgg gac aaa     1056
Thr Met Ala Ser Gln Tyr Arg Asp Asp Arg Gly Arg Glu Trp Asp Lys
                340                 345                 350 att gaa atc aaa taa                                                 1071
Ile Glu Ile Lys
            355

<210> SEQ ID NO 14
<211> LENGTH: 356
```

<212> TYPE: PRT
<213> ORGANISM: lambda phage

<400> SEQUENCE: 14

```
Met Gly Arg Arg Arg Ser His Glu Arg Asp Leu Pro Pro Asn Leu
1               5                   10                  15

Tyr Ile Arg Asn Asn Gly Tyr Tyr Cys Tyr Arg Asp Pro Arg Thr Gly
                20                  25                  30

Lys Glu Phe Gly Leu Gly Arg Asp Arg Arg Ile Ala Ile Thr Glu Ala
            35                  40                  45

Ile Gln Ala Asn Ile Glu Leu Phe Ser Gly His Lys His Lys Pro Leu
50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Glu Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Glu Met Lys Trp Ser Asp Ile
210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335

Thr Met Ala Ser Gln Tyr Arg Asp Asp Arg Gly Arg Glu Trp Asp Lys
            340                 345                 350

Ile Glu Ile Lys
        355
```

<210> SEQ ID NO 15
<211> LENGTH: 219
<212> TYPE: DNA
<213> ORGANISM: lambda phage

```
<220> FEATURE:
<221> NAME/KEY: CDS
<222> LOCATION: (1)..(219)

<400> SEQUENCE: 15 atg tac ttg aca ctt cag gag tgg aac gca cgc cag cga cgt cca aga        48
Met Tyr Leu Thr Leu Gln Glu Trp Asn Ala Arg Gln Arg Arg Pro Arg
1               5                   10                  15 agc ctt gaa aca gtt cgt cga tgg gtt cgg gaa tgc agg ata ttc cca        96
Ser Leu Glu Thr Val Arg Arg Trp Val Arg Glu Cys Arg Ile Phe Pro
                20                  25                  30 cct ccg gtt aag gat gga aga gag tat ctg ttc cac gaa tca gcg gta       144
Pro Pro Val Lys Asp Gly Arg Glu Tyr Leu Phe His Glu Ser Ala Val
            35                  40                  45 aag gtt gac tta aat cga cca gta aca ggt ggc ctt ttg aag agg atc       192
Lys Val Asp Leu Asn Arg Pro Val Thr Gly Gly Leu Leu Lys Arg Ile
        50                  55                  60 aga aat ggg aag aag gcg aag tca tga                                   219
Arg Asn Gly Lys Lys Ala Lys Ser
65                  70

<210> SEQ ID NO 16
<211> LENGTH: 72
<212> TYPE: PRT
<213> ORGANISM: lambda phage

<400> SEQUENCE: 16

Met Tyr Leu Thr Leu Gln Glu Trp Asn Ala Arg Gln Arg Arg Pro Arg
1               5                   10                  15

Ser Leu Glu Thr Val Arg Arg Trp Val Arg Glu Cys Arg Ile Phe Pro
                20                  25                  30

Pro Pro Val Lys Asp Gly Arg Glu Tyr Leu Phe His Glu Ser Ala Val
            35                  40                  45

Lys Val Asp Leu Asn Arg Pro Val Thr Gly Gly Leu Leu Lys Arg Ile
        50                  55                  60

Arg Asn Gly Lys Lys Ala Lys Ser
65                  70

<210> SEQ ID NO 17
<211> LENGTH: 40
<212> TYPE: DNA
<213> ORGANISM: Artificial Sequence
<220> FEATURE:
<223> OTHER INFORMATION: oligonucleotide P1

<400> SEQUENCE: 17
ctagtaagat cttgaagcct gcttttttat actaagttgg                            40

<210> SEQ ID NO 18
<211> LENGTH: 41
<212> TYPE: DNA
<213> ORGANISM: Artificial Sequence
<220> FEATURE:
<223> OTHER INFORMATION: oligonucleotide P2

<400> SEQUENCE: 18
atgatcgaat tcgaaatcaa ataatgattt tattttgact g                          41

<210> SEQ ID NO 19
<211> LENGTH: 41
<212> TYPE: DNA
<213> ORGANISM: Artificial Sequence
<220> FEATURE:
```

```
<223> OTHER INFORMATION: oligonucleotide P3

<400> SEQUENCE: 19
atgccactgc agtctgttac aggtcactaa taccatctaa g                41

<210> SEQ ID NO 20
<211> LENGTH: 46
<212> TYPE: DNA
<213> ORGANISM: Artificial Sequence
<220> FEATURE:
<223> OTHER INFORMATION: oligonucleotide P4

<400> SEQUENCE: 20
accgttaagc tttctagacg ctcaagttag tataaaaaag ctgaac           46

<210> SEQ ID NO 21
<211> LENGTH: 38
<212> TYPE: DNA
<213> ORGANISM: Artificial Sequence
<220> FEATURE:
<223> OTHER INFORMATION: oligonucleotide P5

<400> SEQUENCE: 21
ttcttagacg tcaggtggca cttttcgggg aaatgtgc                    38

<210> SEQ ID NO 22
<211> LENGTH: 37
<212> TYPE: DNA
<213> ORGANISM: Artificial Sequence
<220> FEATURE:
<223> OTHER INFORMATION: oligonucleotide P6

<400> SEQUENCE: 22
taacagagat ctcgcgcaga aaaaaggat ctcaaga                      37

<210> SEQ ID NO 23
<211> LENGTH: 46
<212> TYPE: DNA
<213> ORGANISM: Artificial Sequence
<220> FEATURE:
<223> OTHER INFORMATION: oligonucleotide P7

<400> SEQUENCE: 23
aacagagatc taagcttaga tcctttgcct ggcggcagta gcgcgg           46

<210> SEQ ID NO 24
<211> LENGTH: 35
<212> TYPE: DNA
<213> ORGANISM: Artificial Sequence
<220> FEATURE:
<223> OTHER INFORMATION: oligonucleotide P8

<400> SEQUENCE: 24
ataaactgca gcaaaagag tttgtagaaa cgcaa                        35

<210> SEQ ID NO 25
<211> LENGTH: 36
<212> TYPE: DNA
<213> ORGANISM: Artificial Sequence
<220> FEATURE:
<223> OTHER INFORMATION: oligonucleotide P9

<400> SEQUENCE: 25
agtaattcta gaaagcttaa cacagaaaaa agcccg                      36
```

-continued

```
<210> SEQ ID NO 26
<211> LENGTH: 43
<212> TYPE: DNA
<213> ORGANISM: Artificial Sequence
<220> FEATURE:
<223> OTHER INFORMATION: oligonucleotide P10

<400> SEQUENCE: 26
ctagtaggat ccctgcagtg gtcgaaaaaa aaagcccgca ctg                    43

<210> SEQ ID NO 27
<211> LENGTH: 37
<212> TYPE: DNA
<213> ORGANISM: Artificial Sequence
<220> FEATURE:
<223> OTHER INFORMATION: oligonucleotide P11

<400> SEQUENCE: 27
atcgaggtac cagatctccg gataagtaga cagcctg                          37

<210> SEQ ID NO 28
<211> LENGTH: 32
<212> TYPE: DNA
<213> ORGANISM: Artificial Sequence
<220> FEATURE:
<223> OTHER INFORMATION: oligonucleotide P12

<400> SEQUENCE: 28
gaaggtctag agcgcccggt tgacgctgct ag                               32

<210> SEQ ID NO 29
<211> LENGTH: 1388
<212> TYPE: DNA
<213> ORGANISM: Artificial Sequence
<220> FEATURE:
<223> OTHER INFORMATION: cloned DNA fragment EcoRI-PstI including gene
      for tetracycline resistance (small EcoRI-Van91I fragment of
      pBR322) and transcription terminator ter_thrL

<400> SEQUENCE: 29
gaattctcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
atatgcgttg atgcaatttc tatgcgcacc cgttctcgga gcactgtccg accgctttgg     300
ccgccgccca gtcctgctcg cttcgctact tggagccact atcgactacg cgatcatggc     360
gaccacaccc gtcctgtgga tcctctacgc cggacgcatc gtggccggca tcaccggcgc     420
cacaggtgcg gttgctggcg cctatatcgc cgacatcacc gatggggaag atcgggctcg     480
ccacttcggg ctcatgagcg cttgtttcgg cgtgggtatg gtggcaggcc ccgtggccgg     540
gggactgttg ggcgccatct ccttgcatgc accattcctt gcggcggcgg tgctcaacgg     600
cctcaaccta ctactgggct gcttcctaat gcaggagtcg cataagggag agcgtcgacc     660
gatgcccttg agagccttca acccagtcag ctccttccgg tgggcgcggg gcatgactat     720
cgtcgccgca cttatgactg tcttctttat catgcaactc gtaggacagg tgccggcagc     780
gctctgggtc attttcggcg aggaccgctt tcgctggagc gcgacgatga tcggcctgtc     840
gcttgcggta ttcggaatct tgcacgccct cgctcaagcc ttcgtcactg gtcccgccac     900
caaacgtttc ggcgagaagc aggccattat cgccggcatg gcggccgacg cgctgggcta     960
```

```
cgtcttgctg gcgttcgcga cgcgaggctg gatggccttc cccattatga ttcttctcgc    1020
ttccggcggc atcgggatgc cgcgttgca ggccatgctg tccaggcagg tagatgacga     1080
ccatcaggga cagcttcaag gatcgctcgc ggctcttacc agcctaactt cgatcactgg    1140
accgctgatc gtcacggcga tttatgccgc ctcggcgagc acatggaacg ggttggcatg    1200
gattgtaggc gccgccctat accttgtctg cctccccgcg ttgcgtcgcg gtgcatggag    1260
ccgggccacc tcgacctgaa tggaagccgg cggcacctcg ctaacggatt caccactcca    1320
actagaaagc ttaacacaga aaaagcccg cacctgacag tgcgggcttt tttttttcgac    1380 cactgcag                                                              1388

<210> SEQ ID NO 30
<211> LENGTH: 1162
<212> TYPE: DNA
<213> ORGANISM: Artificial Sequence
<220> FEATURE:
<223> OTHER INFORMATION: cloned DNA fragment containing artificial DNA
      fragment including promoter PA2 (early promoter of phage T7), cat
      gene for chloramphenicol resistance (CmR), transcription
      terminator ter_thrL and attR

<400> SEQUENCE: 30
agatctccgg ataagtagac agcctgataa gtcgcacgaa aaacaggtat tgacaacatg     60
aagtaacatg cagtaagata caaatcgcta ggtaacacta gcagcgtcaa ccgggcgctc    120
tagctagagc caagctagct tggccggatc cgagattttc aggagctaag gaagctaaaa    180
tggagaaaaa aatcactgga tataccaccg ttgatatatc ccaatggcat cgtaaagaac    240
attttgaggc atttcagtca gttgctcaat gtacctataa ccagaccgtt cagctggata    300
ttacggcctt tttaaagacc gtaaagaaaa ataagcacaa gttttatccg gcctttattc    360
acattcttgc ccgcctgatg aatgctcatc cggaattccg tatggcaatg aaagacggtg    420
agctggtgat atgggatagt gttcaccctt gttacaccgt tttccatgag caaactgaaa    480
cgttttcatc gctctggagt gaataccacg acgatttccg gcagtttcta cacatatatt    540
cgcaagatgt ggcgtgttac ggtgaaaacc tggcctattt ccctaaaggg tttattgaga    600
atatgttttt cgtctcagcc aatccctggg tgagtttcac cagttttgat ttaaacgtgg    660
ccaatatgga caacttcttc gcccccgttt tcaccatggg caaatattat acgcaaggcg    720
acaaggtgct gatgccgctg gcgattcagg ttcatcatgc cgtctgtgat ggcttccatg    780
tcggcagaat gcttaatgaa ttacaacagt actgcgatga gtggcagggc ggggcgtaat    840
ttttttaagg cagttattgg tgcccttaaa cgcctggtgc tacgcctgaa taagtgataa    900
taagcggatg aatggcagaa attcgtcgaa gcttaacaca gaaaaaagcc cgcacctgac    960
agtgcgggct ttttttttcg accactgcag tctgttacag gtcactaata ccatctaagt   1020
agttgattca tagtgactgc atatgttgtg ttttacagta ttatgtagtc tgttttttat   1080
gcaaaatcta atttaatata ttgatatttta tatcatttta cgtttctcgt tcagcttttt   1140
tatactaact tgagcgtcta ga                                              1162

<210> SEQ ID NO 31
<211> LENGTH: 27
<212> TYPE: DNA
<213> ORGANISM: Artificial Sequence
<220> FEATURE:
<223> OTHER INFORMATION: oligonucleotide P1'

<400> SEQUENCE: 31
```
ctaatatcga tgaagattct tgctcaa    27

<210> SEQ ID NO 32
<211> LENGTH: 34
<212> TYPE: DNA
<213> ORGANISM: Artificial Sequence
<220> FEATURE:
<223> OTHER INFORMATION: oligonucleotide P2'

<400> SEQUENCE: 32
gcgttgaatt ccatacaacc tccttagtac atgc    34

<210> SEQ ID NO 33
<211> LENGTH: 34
<212> TYPE: DNA
<213> ORGANISM: Artificial Sequence
<220> FEATURE:
<223> OTHER INFORMATION: oligonucleotide P3'

<400> SEQUENCE: 33
gtactagaat tcgtgtaatt gcggagactt tgcg    34

<210> SEQ ID NO 34
<211> LENGTH: 41
<212> TYPE: DNA
<213> ORGANISM: Artificial Sequence
<220> FEATURE:
<223> OTHER INFORMATION: oligonucleotide P4'

<400> SEQUENCE: 34
aatagcctgc agttatttga tttcaatttt gtcccactcc c    41

<210> SEQ ID NO 35
<211> LENGTH: 38
<212> TYPE: DNA
<213> ORGANISM: Artificial Sequence
<220> FEATURE:
<223> OTHER INFORMATION: oligonucleotide P5'

<400> SEQUENCE: 35
ttcttagacg tcaggtggca cttttcgggg aaatgtgc    38

<210> SEQ ID NO 36
<211> LENGTH: 37
<212> TYPE: DNA
<213> ORGANISM: Artificial Sequence
<220> FEATURE:
<223> OTHER INFORMATION: oligonucleotide P6'

<400> SEQUENCE: 36
taacagagat ctagcgcaga aaaaaggat ctcaaga    37

<210> SEQ ID NO 37
<211> LENGTH: 35
<212> TYPE: DNA
<213> ORGANISM: Artificial Sequence
<220> FEATURE:
<223> OTHER INFORMATION: oligonucleotide P7'

<400> SEQUENCE: 37
ataaactgca gcaaaaagag tttgtagaaa cgcaa    35

<210> SEQ ID NO 38
<211> LENGTH: 34
<212> TYPE: DNA
<213> ORGANISM: Artificial Sequence

```
<220> FEATURE:
<223> OTHER INFORMATION: oligonucleotide P8'

<400> SEQUENCE: 38
aacagaagct ttttgcctgg cggcagtagc gcgg                                  34

<210> SEQ ID NO 39
<211> LENGTH: 879
<212> TYPE: DNA
<213> ORGANISM: Artificial Sequence
<220> FEATURE:
<223> OTHER INFORMATION: cloned DNA fragment containing cI repressor
      gene and promoter regions

<400> SEQUENCE: 39
tcgatgaaga ttcttgctca attgttatca gctatgcgcc gaccagaaca ccttgccgat      60
cagccaaacg tctcttcagg ccactgacta gcgataactt tccccacaac ggaacaactc    120
tcattgcatg ggatcattgg gtactgtggg tttagtggtt gtaaaaacac ctgaccgcta    180
tccctgatca gtttcttgaa ggtaaactca tcaccccaa gtctggctat gcagaaatca     240
cctggctcaa cagcctgctc agggtcaacg agaattaaca ttccgtcagg aaagcttggc    300
ttggagcctg ttggtgcggt catggaatta ccttcaacct caagccagaa tgcagaatca    360
ctggcttttt tggttgtgct tacccatctc tccgcatcac ctttggtaaa ggttctaagc    420
tcaggtgaga acatccctgc ctgaacatga aaaaaacag gtactcata ctcacttcta      480 agtgacggct gcatactaac cgcttcatac atctcgtaga tttctctggc gattgaaggg    540
ctaaattctt caacgctaac tttgagaatt tttgcaagca atgcggcgtt ataagcattt    600
aatgcattga tgccattaaa taaagcacca acgcctgact gccccatccc catcttgtct    660
gcgacagatt cctgggataa gccaagttca ttttctttt tttcataaat tgctttaagg     720
cgacgtgcgt cctcaagctg ctcttgtgtt aatggtttct tttttgtgct catacgttaa    780
atctatcacc gcaagggata aatatctaac accgtgcgtg ttgactattt tacctctggc    840
ggtgataatg gttgcatgta ctaaggaggt tgtatggaa                           879

<210> SEQ ID NO 40
<211> LENGTH: 1290
<212> TYPE: DNA
<213> ORGANISM: Artificial Sequence
<220> FEATURE:
<223> OTHER INFORMATION: cloned DNA fragment containing int-xis genes

<400> SEQUENCE: 40
attatttgat ttcaattttg tcccactccc tgcctctgtc atcacgatac tgtgatgcca     60
tggtgtccga cttatgcccg agaagatgtt gagcaaactt atcgcttatc tgcttctcat    120
agagtcttgc agacaaactg cgcaactcgt gaaaggtagg cggatcccct tcgaaggaaa    180
gacctgatgc ttttcgtgcg cgcataaaat accttgatac tgtgccggat gaaagcggtt    240
cgcgacgagt agatgcaatt atggtttctc cgccaagaat ctctttgcat ttatcaagtg    300
tttccttcat tgatattccg agagcatcaa tatgcaatgc tgttgggatg caatttta      360 cgcctgtttt gctttgctcg acataaagat atccatctac gatatcagac cacttcattt    420
cgcataaatc accaactcgt tgcccggtaa caacagccag ttccattgca agtctgagcc    480
aacatggtga tgattctgct gcttgataaa ttttcaggta ttcgtcagcc gtaagtcttg    540
atctccttac ctctgatttt gctgcgcgag tggcagcgac atggtttgtt gttatatggc    600
cttcagctat tgcctctcgg aatgcatcgc tcagtgttga tctgattaac ttggctgacg    660
```

-continued

```
ccgccttgcc ctcgtctatg tatccattga gcattgccgc aatttctttt gtggtgatgt      720
cttcaagtgg agcatcaggc agaccctcc ttattgcttt aattttgctc atgtaattta       780
tgagtgtctt ctgcttgatt cctctgctgg ccaggatttt ttcgtagcga tcaagccatg      840
aatgtaacgt aacggaatta tcactgttga ttctcgctgt cagaggcttg tgtttgtgtc      900
ctgaaaataa ctcaatgttg gcctgtatag cttcagtgat tgcgattcgc ctgtctctgc      960
ctaatccaaa ctctttaccc gtccttgggt ccctgtagca gtaatatcca ttgtttctta     1020
tataaaggtt aggggtaaa tcccggcgct catgacttcg ccttcttccc atttctgatc      1080
ctcttcaaaa ggccacctgt tactggtcga tttaagtcaa cctttaccgc tgattcgtgg     1140
aacagatact ctcttccatc cttaaccgga ggtgggaata tcctgcattc ccgaacccat     1200
cgacgaactg tttcaaggct tcttggacgt cgctggcgtg cgttccactc ctgaagtgtc     1260
aagtacatcg caaagtctcc gcaattacac                                      1290

<210> SEQ ID NO 41
<211> LENGTH: 351
<212> TYPE: DNA
<213> ORGANISM: Artificial Sequence
<220> FEATURE:
<223> OTHER INFORMATION: ter_rrnB fragment (complement)

<400> SEQUENCE: 41
caaaaagagt ttgtagaaac gcaaaaaggc catccgtcag gatggccttc tgcttaatttt     60 gatgcctggc agtttatggc gggcgtcctg cccgccaccc tccgggccgt tgcttcgcaa     120
cgttcaaatc cgctcccggc ggatttgtcc tactcaggag agcgttcacc gacaaacaac     180
agataaaacg aaaggcccag tctttcgact gagcctttcg ttttatttga tgcctggcag     240
ttccctactc tcgcatgggg agaccccaca ctaccatcgg cgctacggcg tttcacttct     300
gagttcggca tggggtcagg tgggaccacc gcgctactgc cgccaggcaa a             351
```

METHOD FOR PRODUCING L-LYSINE OR L-THREONINE

This application claims priority under 35 U.S.C. §119(a) to Japanese patent application 2003-202842, filed Jul. 29, 2003, and is a continuation under 35 U.S.C. §120 of PCT patent application PCT/JP2004/011220, filed Jul. 29, 2004, both of which are incorporated by reference in their entireties. The Sequence Listing on Compact Disk filed herewith is also hereby incorporated by reference in its entirety (File Name: US-177 Seq List; File Size: 53 KB; Date Created: Jan. 3, 2006).

BACKGROUND OF THE INVENTION

1. Technical Field

The present invention relates to a method for producing L-lysine or L-threonine using an *Escherichia* bacterium. L-Lysine and L-threonine are known as essential amino acids, and are useful as components in pharmaceutical compositions and diverse nutritive mixtures, such as additives to animal fodder.

2. Background Art

L-amino acids, such as L-threonine and L-lysine, are industrially produced by fermentation using L-amino acid-producing bacteria, such as coryneform or *Escherichia* bacteria which have the ability to produce L-amino acids. To improve productivity, a strain isolated from nature, an artificial mutant thereof, or a recombinant in which the L-amino acid biosynthetic enzyme activity is increased by gene recombination has been used as the L-amino acid-producing bacterium. The method for producing L-lysine is exemplified in Japanese Patent Application Laid-Open No. 10-165180, Japanese Patent Application Laid-Open No. 11-192088, Japanese Patent Application Laid-Open No. 2000-253879, and Japanese Patent Application Laid-Open No. 2001-57896. The method for producing L-threonine is exemplified in Japanese Patent Application Laid-Open No. 5-304969, International Publication No. WO98/04715, Japanese Patent Application Laid-Open No. 5-227977, and U.S. Patent Application Publication No. 2002/0110876.

Methods for increasing the ability to produce amino acids such as L-threonine and L-lysine include a method for increasing energy efficiency by modifying a respiratory chain pathway (Japanese Patent Application Laid-Open No. 2002-17363), and a method for increasing an ability to produce nicotinamide adenine dinucleotide phosphate by amplifying a nicotinamide nucleotide transdehydrogenase (Japanese Patent No. 2817400), as well as a method of increasing an expression amount of an enzyme of the endogenous biosynthetic pathway.

In addition, methods for modifying common pathways of amino acid biosynthetic systems are known and include modifying anaplerotic pathways of L-amino acid-producing bacteria, such as an L-lysine-producing coryneform bacterium in which pyruvate carboxylase activity is increased (Japanese Patent Application Laid-Open No. 2002-508921), an L-lysine-producing *Escherichia* bacterium which is deficient in pyruvate kinase (International Publication No. WO03/008600), and an L-lysine-producing coryneform bacterium which is deficient in malate quinine oxidoreductase (U.S. Patent Application Publication No. 2003/0044943).

A malic enzyme is one of the anaplerotic pathway enzymes. In the *Escherichia* bacteria, it is known that each of the sfcA and b2463 genes encodes the malic enzyme (van der Rest, M. E., Frank C., Molenaar, D. J., J. Bacteriol., 182(24):6892-6899, 2000). However, whether or not a decrease in the activity of the malic enzymes encoded by the sfcA and b2463 genes is effective for enhancing L-lysine or L-threonine production has not been reported.

A metabolic flux analysis, which is also referred to as a flux balance analysis, is a technique for predicting intracellular metabolic flux distributions by construction of a stoichiometric model of intracellular biochemical reactions and linear optimization. This technique has been used in research into the abilities of biochemical reaction systems in microorganisms or for predicting intracellular metabolic flux distributions under different external conditions (Varma, A. and Palsson, B. O., Appl. Environ. Microbiol. 60:3724-3731, 1994, Schilling, C. H., et al., Biotechnol. Prog., 15:288-295, 1999, and Schilling, C. H., et al., Biotechnol. Prog., 15:296-303, 1999). It has also been reported that a stoichiometric model was constructed for *Escherichia coli* (Pramanik, J. and Keasling, J. D., Biotechnol. Bioeng., 56:398-421, 1997, and Ibarra, R. U., et al., Nature, 420:186-189, 2002). Also known is an example of using such a stoichiometric model in metabolic engineering for lysine production for *Corynebacterium glutamicum,* which is used in amino acid production (Vallino, J. J. and Stephanopoulos, G., Biotechnol. Bioeng., 41:633-646, 1993). In addition, a large number of theoretical or experimental methods for metabolic flux analyses and their applications have been reported (Wiechert, W., Journal of Biotechnology, 94:37-63, 2002, Wiechert, W., Metabolic Engineering, 3:195-205, 2001, International Publication No. WO00/46405, International Publication No. WO02/061115, and International Publication No. WO02/055995). International Publication No. WO00/46405 discloses a method for predicting a gene required for growth based on a stoichiometric model. International Publication No. WO02/061115 discloses a technique for genetically and evolutionarily changing cells to impart optimal functions to the cells. Furthermore, International Publication No. WO02/055995 discloses a method for applying limitations of qualitative kinetic information, limitations of qualitative control information, and limitations based on DNA microarray experimental data under different conditions, to a stoichiometric model. Although all of these are methods for predicting more desirable intracellular metabolic flux distributions, no method has been disclosed for theoretically predicting a specific flux as a target for directly improving cellular substance production.

SUMMARY OF THE INVENTION

The present invention provides an *Escherichia* bacterium which has an improved ability to produce L-lysine or L-threonine, and a method for producing L-lysine or L-threonine using the bacterium.

The inventors of the present invention assiduously studied to solve the problem and as a result, they found that production of a metabolic flux affecting substance production could be determined by (1) selecting the same number of free fluxes as the degree of freedom of a stoichiometric matrix calculated based on formulas of biochemical reactions from a substrate through a desired produced substance, (2) calculating metabolic flux distributions from random combinations of the free fluxes in a number sufficient for a statistical analysis based on the stoichiometric matrix, and (3) obtaining a regression equation which includes a minimum number of free fluxes which correlate to the substance production from the calculated metabolic flux distributions based on statistical analysis.

Determination of the metabolic fluxes of an L-lysine or L-threonine-producing bacterium by this method has revealed that a modification so that a malic enzyme does not function normally is effective for increasing the productivity of the bacterium. The present invention was accomplished based on the aforementioned findings and provides the following:

It is an object of the present invention to provide an *Escherichia* bacterium which has an ability to produce L-lysine or L-threonine, and wherein said bacterium is modified so that a malic enzyme does not function normally in the bacterium.

It is a further object of the present invention to provide the bacterium as described above, wherein a gene encoding said malic enzyme on the bacterial chromosome is mutated and/or an expression control sequence thereof is mutated so that the malic enzyme does not function normally in the bacterium.

It is a further object of the present invention to provide the bacterium as described above, wherein said malic enzyme does not function normally due to disruption of a gene which encodes said malic enzyme on the bacterial chromosome.

It is a further object of the present invention to provide the bacterium as described above, wherein the gene encoding said malic enzyme comprises sfcA.

It is a further object of the present invention to provide the bacterium as described above, wherein the gene encoding said malic enzyme comprises b2463.

It is a further object of the present invention to provide the bacterium as described above, wherein said malic enzyme is selected from the group consisting of:

(A) a protein comprising the amino acid sequence shown in SEQ ID NO: 6, and (B) a protein comprising an amino acid sequence comprising substitution, deletion, insertion, or addition of one or several amino acid residues in the amino acid sequence shown in SEQ ID NO: 6, wherein said protein has a malic enzyme activity.

It is a further object of the present invention to provide the bacterium as described above, wherein said malic enzyme is selected from the group consisting of:

(C) a protein comprising the amino acid sequence shown in SEQ ID NO: 8, and (D) a protein comprising an amino acid sequence comprising substitution, deletion, insertion or addition of one or several amino acid residues in the amino acid sequence shown in SEQ ID NO: 8, wherein said protein has a malic enzyme activity.

It is a further object of the present invention to provide the bacterium as described above, wherein a gene encoding said malic enzyme is a DNA selected from the group consisting of:

(a) a DNA comprising a nucleotide sequence shown in SEQ ID NO: 5, (b) a DNA which hybridizes with the nucleotide sequence shown in SEQ ID NO: 5, or a probe which can be prepared from the nucleotide sequence, wherein said hybridization occurs under stringent conditions, and wherein said DNA encodes a protein having a malic enzyme activity.

It is a further object of the present invention to provide the bacterium as described above, wherein a gene encoding the malic enzyme is a DNA selected from the group consisting of:

(a) a DNA comprising a nucleotide sequence shown in SEQ ID NO: 7, and (b) a DNA which hybridizes with the nucleotide sequence shown in SEQ ID NO: 7, or a probe which can be prepared from the nucleotide sequence, wherein said hybridization occurs under stringent conditions, and wherein said DNA encodes a protein having a malic enzyme activity.

It is a further object of the present invention to provide a method for producing L-lysine or L-threonine, comprising culturing the bacterium as described above in a medium so to produce and secrete said L-lysine or L-threonine, and collecting the L-lysine or L-threonine from the medium.

DESCRIPTION OF THE PREFERRED EMBODIMENTS

Figure 1:
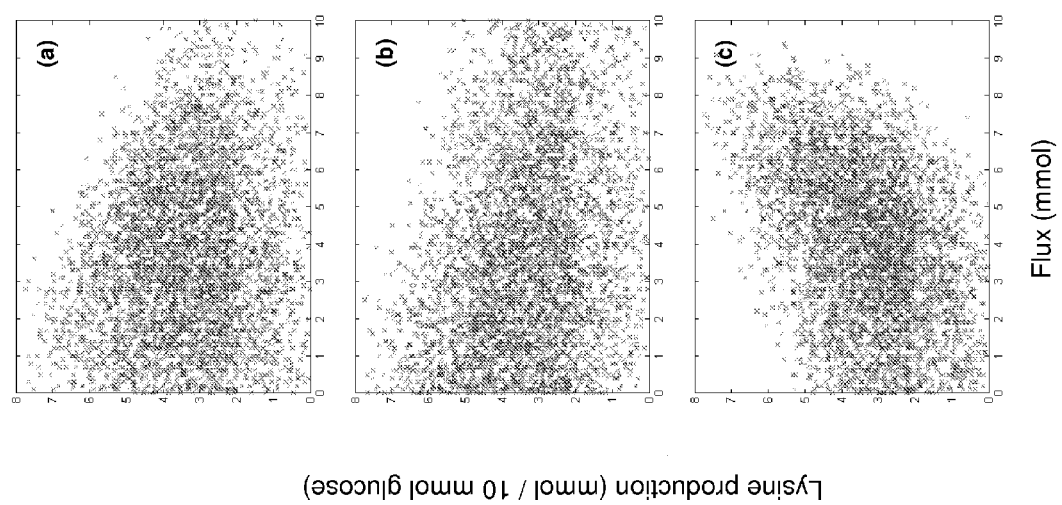
FIG. 1 is a plot showing lysine production as a function of different values of free fluxes by using a dataset of 5000 random flux distributions. The lysine yields are shown for (a) isocitrate lyase flux, (b) malic enzyme flux, and (c) PEP carboxylase flux.

Hereinafter, the present invention will be explained in detail.

<1> *Escherichia* Bacterium of the Present Invention

The *Escherichia* bacterium of the present invention is a bacterium belonging to the genus *Escherichia* which has an ability to produce L-lysine or L-threonine and which is modified so that a malic enzyme does not function normally. The *Escherichia* bacterium of the present invention may have an ability to produce either L-lysine or L-threonine, or may have an ability to produce both L-lysine and L-threonine.

A parent strain belonging to the genus *Escherichia* which is used for obtaining the *Escherichia* bacterium of the present invention includes, but is not limited to those described in a book written by Neidhardt et al. (Neidhardt, F. C. et al., *Escherichia coli* and *Salmonella Typhimurium*, American Society for Microbiology, Washington D. C., 1029, table 1). For example, the parent strain may be *Escherichia coli*. The *Escherichia coli* maybe *Escherichia coli* W3110 (ATCC 27325) or *Escherichia coli* MG1655 (ATCC 47076), which are both derived from the prototype wild strain K12.

One may obtain these strains from the American Type Culture Collection (Address: 12301 Parklawn Drive, Rockville, Md. 20852, United States of America), for example. Registration numbers are assigned to strains, and one may request the desired strain by its registration number. The registration numbers for each strain are listed in the American Type Culture Collection catalog.

<1>-1. Imparting the Ability to Produce L-Lysine or L-Threonine

A method for imparting the ability to produce L-lysine or L-threonine to the *Escherichia* bacterium is described below. The phrase "ability to produce L-lysine" as used herein means an ability to produce and cause accumulation of, or secrete, L-lysine into a medium, i.e. free extracellular L-lysine, when the bacterium is cultured in the medium. In particular, the phrase "ability to produce L-lysine" means an ability to cause accumulation of more L-lysine as compared with a wild-type, or parent strain.

The phrase "ability to produce L-threonine" as used herein means an ability to produce and cause accumulation of, or secrete, L-threonine in a medium, i.e. free extracellular L-threonine, when the bacterium is cultured in the medium. In particular, this phrase means an ability to cause accumulation of more L-threonine as compared with a wild-type, or parent strain.

To impart L-lysine or L-threonine-producing ability, conventional methods for breeding *Escherichia* bacteria and coryneform bacteria can be used, such as methods for obtaining auxotrophic mutant strains, strains resistant to analogues, or metabolic control mutant strains which have an ability to produce L-lysine or L-threonine, and methods for producing recombinant strains wherein L-lysine or L-threonine biosynthetic enzyme activities are increased. In the breeding of L-lysine or L-threonine-producing bacteria, characteristics such as auxotrophy, analogue resistance, and metabolic control mutations may be imparted alone or in combination.

The L-lysine or L-threonine biosynthetic enzyme activity or activities may be increased alone or in combination. Furthermore, imparting characteristics such as auxotrophy, analogue resistance, and metabolic control mutations may be combined with increasing the L-lysine and/or L-threonine biosynthesis enzyme activity.

Examples of methods for imparting or increasing the ability to produce L-lysine or L-threonine by increasing the L-lysine or L-threonine biosynthetic enzyme activity are described below. Increasing the enzyme activity may be performed by, for example, introducing a mutation to a gene encoding the enzyme or amplifying the gene so that an intracellular activity of the enzyme is increased. These may be performed by gene recombination.

Genes encoding the L-threonine biosynthetic enzymes include, but are not limited to, the aspartokinase III gene (lysC), the aspartate semialdehyde dehydrogenease gene (asd), the aspartokinase I encoded by the thr operon (thrA), the homoserine kinase gene (thrB), and the threonine synthase gene (thrC). The abbreviated symbol of the gene is shown in parenthesis. Two or more of these genes may be introduced. The L-threonine biosynthetic enzyme gene may be introduced into an *Escherichia* bacterium of which threonine degradation is suppressed. An *Escherichia* bacterium of which threonine degradation is suppressed is exemplified by the strain TDH6, which is deficient in a threonine dehydrogenase activity (Japanese Patent Application Laid-Open No. 2001-346578).

Genes encoding the L-lysine biosynthetic enzymes include, but are not limited to diaminopimelate pathway enzymes, such as the dihydrodipicolinate synthase gene (dapA), the aspartokinase gene (lysC), the dihydrodipicolinated reductase gene (dapB), the diaminopimelate decarboxylase gene (lysA), the diaminopimelate dehydrogenase gene (ddh) (all of the foregoing; International Publication No. 96/40934), the phosphoenolpyrvate carboxylase gene (ppc) (Japanese Patent Application Laid-Open No. 60-87788), the aspartate aminotransferase gene (aspC) (Japanese Patent Publication No. 6-102028), the diaminopimelate epimerase gene (dapF) (Japanese Patent Application Laid-Open No. 2003-135066), and the aspartate semialdehyde dehydrogenease gene (asd) (International Publication No. 00/61723), and the aminoadipate pathway enzymes, such as the homoaconitate hydratase gene (Japanese Patent Application Laid-Open No. 2000-157276).

Furthermore, the bacterium of the present invention may have decreased activity of an enzyme that catalyzes a reaction for generating a compound other than L-lysine by branching off from the biosynthetic pathway of L-lysine, or may be deficient in such an enzyme. Enzymes that catalyze a reaction for generating a compound other than L-lysine by branching off from the biosynthetic pathway of L-lysine include homoserine dehydrogenase and lysine decarboxylase. Strains having decreased activities of the enzymes are described in WO95/23864 and WO 96/178930.

Increasing the activity of the enzyme encoded by the gene can be achieved by amplifying the L-lysine or L-threonine biosynthetic gene with a plasmid which is autonomously replicable in *Escherichia* bacteria, for example. The biosynthetic gene may be integrated into the bacterial chromosome. It can be also be achieved by introducing a gene which includes a mutation that causes the activity of the enzyme encoded by the gene to increase. Examples of such a mutation include mutating a promoter sequence, so that the transcription amount of the gene increases, and mutation in the coding region of the gene, so that a specific activity of the enzyme protein increases.

Other than gene amplification as described above, gene expression can be amplified by replacing an expression control sequence, such as a promoter of the gene on the chromosomal DNA or plasmid, with a stronger one (International Publication No. WO 00/18935). Strong promoters are known and include, for example, the lac promoter, the trp promoter, the trc promoter, the tac promoter, and the $P_R$ promoter of lambda phage. Expression of the gene may be increased by replacing the endogenous promoter on either the chromosome or plasmid with a stronger one, or by modifying the endogenous promoter. Modifying the expression control sequence can be combined with increasing the copy number of the gene.

Examples of *Escherichia* bacteria to which the ability to produce L-lysine or L-threonine can be imparted, which can be used in the present invention, are shown below. However, the bacterium of the present invention is not limited to these examples, but encompasses any bacteria which has the ability to produce L-lysine or L-threonine.

Specific examples of strains resistant to analogues or metabolic control mutant strains which have an ability to produce L-lysine include *Escherichia coli* AJ11442 (FERM BP-1543, NRRL B-12185; Japanese Patent Application Laid-Open No. 56-18596 and U.S. Pat. No. 4,346,170) and *Escherichia coli* VL611. Strain WC196 may be used as an L-lysine-producing bacterium of *Escherichia coli* (International Publication No. WO96/17930). The WC196 strain was bred by imparting AEC (S-(2-aminoethyl)cysteine) resistance to strain W3110, which was derived from *Escherichia coli* K-12. This strain was designated *Escherichia coli* AJ13069, and deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. It was converted to an international deposit under the provisions of the Budapest Treaty on Sep. 29, 1995, and received an accession number of FERM BP-5252.

Examples of *Escherichia* bacteria having an ability to produce L-threonine include a L-threonine-producing mutant strain which is resistant to 6-dimethylaminopurine (Japanese Patent Application Laid-Open No. 5-304969), recombinant *Escherichia coli* strains such as a strain in which a threonine biosynthetic gene having an introduced mutation which causes excess production of L-threonine biosynthetic enzyme is amplified on a plasmid (Japanese Patent Publication No. 1-29559, and Japanese Patent Application Laid-Open No. 5-227977), a strain in which a threonine operon is amplified on a plasmid (Japanese Patent Application Laid-Open No. 2-109985), and a strain in which genes encoding pyruvate carboxylase and nicotinamide nucleotide transhydrogenase are amplified (Japanese Patent Application Laid-Open No. 2002-51787).

*Escherichia coli* VKPM B-3996 (U.S. Pat. No. 5,175, 107) is also encompassed by the present invention. The VKPM B-3996 strain was deposited at Russian National Collection of Industrial Microorganisms (VKPM), GNII Genetika) on Nov. 19, 1987 and received an accession number of VKPM B-3996. The VKPM B-3996 harbors plasmid pVIC40 (International Publication No. WO 90/04636), which is produced by inserting threonine biosynthetic genes (threonine operon: thrABC) into a broad-host range vector, for example, plasmid pAYC32 (Chistoserdov, A. Y., Tsygankov, Y. D., Plasmid, 1986, 16, 161-167). In the pVIC40, the feedback inhibition by L-threonine of aspartokinase I-homoserine dehydrogenase I encoded by thrA in the threonine operon is desensitized.

Furthermore, *Escherichia coli* B-5318 (European Patent No. 0593792) is encompassed by the present invention. The B-5318 strain was deposited at Russian National Collection of Industrial Microorganisms (VKPM), GNII Genetika) on Nov. 19, 1987 and received an accession number of VKPM B-5318. The VKPM B-5318 is prototrophic with regard to isoleucine and harbors a recombinant plasmid DNA. This plasmid is constructed so that the threonine operon, including the threonine biosynthetic genes, is deficient in an attenuation region, for example, the endogenous transcription regulation region. The operon is positioned downstream from lambda-phage temperature-sensitive C1 repressor, the $P_R$ promoter, and the N-terminal of Cro protein, and is constructed so that the expression of the threonine biosynthetic genes is under the control of a lambda-phage repressor and promoter.

<2> Construction of *Escherichia* Bacterium of the Present Invention

The *Escherichia* bacterium of the present invention is a bacterium belonging to the genus *Escherichia* which has an ability to produce L-lysine or L-threonine, and which is modified so that a malic enzyme does not function normally.

During the breeding of the *Escherichia* bacterium of the present invention, either imparting the ability to produce L-lysine or L-threonine, or imparting a mutation which causes the malic enzyme (EC 1.1.1.38, EC 1.1.1.40) to not function normally may be initially performed. Also, an *Escherichia* bacterium having the ability to produce L-lysine or L-threonine may be modified so that the malic enzyme does not function normally, and the ability to produce L-lysine or L-threonine may be imparted to an *Escherichia* bacterium in which the malic enzyme does not function normally yet.

The phrase "activity of a malic enzyme" means an activity to catalyze a reversible reaction to produce carbondioxide and pyruvate from malate. Malic enzymes which use NAD (EC 1.1.1.38) and NADP (EC 1.1.1.40) as coenzymes are known. (EC 1.1.1.38(S)-malate+NAD+=pyruvate+$CO_2$+NADH+$H^+$) (EC 1.1.1.40(S)-malate+$NADP^+$=pyruvate+$CO_2$+NADPH+$H^+$). The malic enzyme is also called "malate dehydrogenase", or "malate oxidoreductase".

The phrase "modified so that a malic enzyme does not function normally in a bacterium" means that it is modified so that the function of the malic enzyme should be eliminated or the activity of the malic enzyme should be reduced or attenuated compared with an unmodified strain such as a wild-type (parent) strain. The state where the malic enzyme does not function normally may be, for example, when transcription or translation of the gene encoding the malic enzyme is inhibited, and hence the gene product thereof, the malic enzyme is not produced or the production reduced, or a state where the gene encoding said malic enzyme on the bacterial chromosome is mutated and/or an expression control sequence thereof is mutated, and thus the activity of the malic enzyme is reduced or eliminated. Examples of the *Escherichia* bacterium in which the malic enzyme does not function normally include, typically, a gene-disrupted strain in which the gene encoding the malic enzyme on the bacterial chromosome is disrupted by genetic recombination technique, and a mutant strain in which an expression regulatory sequence or a coding region of the malic enzyme gene is mutated, and therefore a functional malic enzyme is no longer produced.

The phrase "modified so that an activity of a malic enzyme is attenuated" means that the activity of the malic enzyme is reduced compared with that of an unmodified strain, for example, a wild-type (parent) strain of *Escherichia* bacteria. The activity of the malic enzyme preferably is reduced to not more than 50%, more preferably not more than 30%, still more preferably not more than 10% per cell compared with the unmodified strain.

Examples of the *Escherichia* bacterium which can act as a control include *Escherichia coli* W3110 (ATCC 27325) and *Escherichia coli* MG1655 (ATCC 47076). These wild-type strains are derived from the prototype wild-type strain K12. Malic enzyme activity, using NAD as coenzyme, can be determined according to the method of Korkes, S., et al. (Korkes, S. et al., (1950) J. Biol. Chem. 187, 891-905). Malic enzyme activity using NADP as coenzyme can be determined according to the method of Ochoa, S. (Ochoa, S. et al (1947) J. Biol. Chem. 167, 871-872).

The term "attenuation" includes, but is not limited to, the complete elimination of the activity. Malic enzyme activity using NAD or NADP as coenzymes may be attenuated each individually, or together. It is sufficient for the present invention that the *Escherichia* bacterium has the attenuated malic enzyme activity as compared with a wild-type or unmodified strain. However, it is preferred that the *Escherichia* bacterium of the present invention also has an increased ability to cause accumulation, or secrete L-lysine or L-threonine as compared to the wild-type or unmodified strain, and/or improved L-lysine or L-threonine productivity because of good growth, namely improved cell-subtracted yield.

The malic enzyme of the present includes the protein having the amino acid sequence shown in SEQ ID NO: 6 or 8. The malic enzyme may be a variant of the amino acid sequence shown in SEQ ID NO: 6 or 8, in that it may include substitution, deletion, insertion or addition of one or several amino acid residues in the amino acid sequence shown in SEQ ID NO: 6 or 8, provided that it has a malic enzyme activity. "Several" as used herein, means, for example, 2 to 20, preferably 2 to 10, more preferably 2 to 5.

The substitution, deletion, insertion or addition of one or several amino acid residues should be conservative mutation(s) so that the malic enzyme activity is maintained. The representative conservative mutation is a conservative substitution. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The phrase "modified so that a malic enzyme does not function normally" can mean to decrease the number of malic enzyme molecules per cell and to decrease the malic enzyme activity per molecule. Specifically, the modification may be performed by making a gene encoding the malic enzyme on the chromosome deficient, or modifying an expression control sequence such as a promoter or Shine-Dalgarno (SD) sequence. Also, the modification may be performed by introducing substitution of an amino acid (missense mutation), or a stop codon (nonsense mutation) to a coding region, or introducing insertion or deletion of 1 to 2 bases to a coding region (frameshift mutation) or deleting part of the gene (Journal of Biological Chemistry 272:8611-8617(1997)).

Examples of a malic enzyme gene (mez gene) on the chromosome include the sfcA gene, such as a DNA having the nucleotide sequence shown in SEQ ID NO: 5. This DNA encodes the enzyme which uses NAD as a coenzyme. Another example is the b2463 gene, such as a DNA having the nucleotide sequence shown in SEQ ID NO: 7. This DNA encodes the enzyme which uses NADP as a coenzyme.

The mez gene may be a DNA which hybridizes with the nucleotide sequence shown in SEQ ID NO: 5 or 7, or a probe which can be prepared from the nucleotide sequence under stringent conditions, provided that it encodes a protein which has malic enzyme activity. "Stringent conditions" include those under which a specific hybrid is formed and a non-specific hybrid is not formed. For example, stringent conditions are exemplified by washing one time, preferably two or three times at a salt concentration corresponding to 1×SSC, 0.1% SDS, preferably 0.1×SSC, 0.1% SDS at 60° C. The length of the probe may be suitably selected depending on the hybridization conditions, and is usually 100 bp to 1 kbp.

The gene encoding the malic enzyme (sfcA, b2643) can be obtained by PCR using the chromosome of *Escherichia coli* as a template, and oligonucleotides synthesized based on the following sequences of *Escherichia coli* registered in GenBank as primers: sfcA: AAC74552. NAD-linked malate . . . [gi:1787754], complement of AE000245.1:1208 . . . 2932, b2643: AAC75516. putative multimod . . . [gi:1788806], complement of AE000333.1: 141 . . . 2420.

Chromosomal DNA can be prepared from a bacterium for use as a DNA donor by, for example, the method of Saito and Miura (refer to H. Saito and K. Miura, Biochem. Biophys. Acta, 72, 619 (1963), Text for Bioengineering Experiments, Edited by the Society for Bioscience and Bioengineering, Japan, pp. 97-98, Baifukan, 1992) or the like.

The sfcA or b2643 gene prepared as described above, or a part thereof, can be used for gene disruption. The gene used for gene disruption is sufficient if it has a degree of homology that allows for homologous recombination with the sfcA or b2463 gene on the *Escherichia* bacterium chromosome. Therefore, such a homologous gene can be used. The degree of homology that should allow for homologous recombination is preferably 70% or more, more preferably 80% or more, still more preferably 90% or more, and particularly preferably 95% or more. Also, homologous recombination may occur if a DNA which is hybridizable with the gene under stringent conditions is used. The "stringent conditions" are conditions under which a specific hybrid is formed, and a non-specific hybrid is not formed. For example, stringent conditions are exemplified by washing one time, preferably two or three times at a salt concentration corresponding to 1×SSC, 0.1% SDS, preferably 0.1×SSC, 0.1% SDS, at 60° C.

The sfcA or b2463 gene can be disrupted by, for example, preparing, from the gene as described above, a deletion-type sfcA or b2463 gene in which a partial sequence is deleted so that a malic enzyme which functions normally is not produced. This deletion-type gene, or a DNA which includes the gene, can then be transformed into an *Escherichia* bacterium, and recombination caused between the deletion-type gene and the gene on the chromosome. The gene disruption by the gene substitution using homologous recombination has already been established, and is exemplified by using a linear DNA represented by a method developed by Datsenko K. A., and Wanner B. L. (Proc. Natl. Acad. Sci. USA, 2000, 97, 6640-6645) also called as a "Red-driven integration", and a method using a plasmid harboring a temperature-sensitive replication origin (U.S. Pat. No. 6,303,383 and Japanese Patent Application Laid-Open No. 5-7491). The gene disruption by the gene substitution using homologous recombination can be also performed by using a plasmid which doesn't have replication ability in a host.

In addition, a method based on a combination of the method called "red-driven integration" and an excision system derived from lambda phage (J. Bacteriol. 2002 September; 184(18):5200-3. Interactions between integrase and excisionase in the phage lambda excisive nucleoprotein complex Cho EH, Gumport RI, Gardner JF) can be used as the method for disrupting a gene on a chromosome.

According to the red-driven integration method, a gene-disrupted strain can be constructed in one step by using a PCR product, which is obtained using synthetic oligonucleotides as primers which are designed to comprise part of a targeted gene at its 5' terminus, and part of an antibiotic resistance gene at its 3' terminus. Furthermore, the integrated antibiotic resistance gene can be removed by introducing attL and attR, which are attachment sites of lambda phage and the PCR product, and combining the excision system derived from lambda phage with the red-driven integration method.

Specifically, a strain in which the targeted gene is disrupted and the antibiotic resistance gene is removed can be obtained by the following method.

A linear DNA cassette comprising an antibiotic resistance gene, attachment sites of lambda phage and a target gene is initially prepared. This is usually prepared by PCR using a suitably-prepared template.

A template in which attL and attR (SEQ ID NO: 9 (GenBank accession No. M12458 and SEQ ID NO: 10 (GenBank accession No. M12459)) which are attachment sites of lambda phage, are inserted at respective terminals of an antibiotic resistance gene is used as a template of the linear DNA cassette. The template may be a plasmid, a gene inserted on a chromosome, or a synthetic oligonucleotide. While the antibiotic resistance gene is preferably a chloramphenicol resistance gene, a streptomycin resistance gene, or an ampicillin resistance gene, any antibiotic resistance gene can be used provided that the gene functions as an antibiotic resistance gene in *Escherichia* bacteria and is different from a marker gene which may be contained in two helper plasmids as described below. To easily confirm the acquisition of the antibiotic resistance, the antibiotic resistance gene which is employed can be one whereby the expression amount is increased by replacing a promoter sequence and the like, or one in which a mutation is introduced in its structural gene sequence so that an enzyme activity is increased. The linear DNA cassette is prepared in the following order from the 5' terminus: (targeted gene 5' sequence)-(attL)-(antibiotic resistance gene)-(attR)-(targeted gene 3' sequence).

The linear DNA cassette is integrated into the chromosome. As a helper plasmid for integrating the linear DNA cassette into chromosome, pKD46 can be used (Proc. Natl. Acad. Sci. USA, 2000, 97, 6640-6645). pKD46 shows temperature-sensitive replication and ampicillin resistance, and includes a 2,154 nt DNA fragment of lambda phage (GenBank/EMBL accession No. J02459, 31088-33241), which contains the genes (γ, β, and exo genes) encoding Red recombinase of the λ Red homologous recombination system and which is under the control of the arabinose-inducible $P_{araB}$ promoter.

pKD46 can be introduced into a host by electroporation. The pKD46-amplified strain is cultured with arabinose. The linear DNA cassette is introduced at the logarithmic growth phase and incubated at a high temperature to obtain a gene-disrupted strain which is resistant to an antibiotic by the antibiotic resistance gene in the linear DNA cassette. The confirmation of the gene disruption can be made by PCR or measurement of the concentration of L-lysine or L-threonine produced by the strain.

A helper plasmid for excising the antibiotic resistance gene is then introduced. The helper plasmid harbors a gene encoding integrase (Int) (SEQ ID NO: 13, GenBank accession No. J02459. B [gi:215104]) and a gene encoding excisionase (Xis) (SEQ ID NO: 15, GenBank accession No. J02459 [gi:215104]) of lambda phage and shows temperature-sensitive replication. By introduction of the helper plasmid, recombination occurs due to recognition of attL (SEQ ID NO: 11) and attR (SEQ ID NO: 12) on the chromosome. The antibiotic resistance gene between attL and attR is excised and as a result, a structure that contains only the attL or attR sequence remains on the chromosome. By incubating at a high temperature, the helper plasmid is lost. Thus a strain in which the targeted gene is disrupted and the antibiotic gene is eliminated can be obtained.

Other than genetic engineering methods, the method for modifying the bacterium so that a malic enzyme does not function normally may be exemplified by a method of treating an *Escherichia* bacterium with UV irradiation or a mutagenic agent usually used for mutagenesis, such as N-methyl-N'-nitro-N-nitrosoguanidine and nitric acid, followed by selection of the bacterium with the attenuated activity of the malic enzyme.

The present invention has been achieved based on the metabolic flux information. This information was calculated by the following method for determining the metabolic flux affecting substance production using cells. However, the present invention is not limited to the method for obtaining such information, that is, the determination method.

The method for determining a metabolic flux affecting substance production using cells, includes the steps of:

1) creating a stoichiometric matrix based on the formulas of biochemical reactions of a substrate through a desired substance, 2) selecting the same number of independent metabolic fluxes from all metabolic fluxes as the degree of freedom of the stoichiometric matrix as free fluxes, 3) creating a sufficient number of random combinations of the free fluxes for a statistical analysis and calculating a metabolic flux distribution from each created combination based on the stoichiometric matrix, 4) obtaining a regression equation, including a minimum number of free fluxes that shows a correlation with substance production from the calculated metabolic flux distributions by a multivariate statistical analysis, and 5) determining at least one metabolic flux affecting substance production based on a coefficient in the obtained regression equation.

The metabolic flux used in the present invention is expressed as a metabolic reaction rate (flux) derived from a stoichiometric model of intracellular biochemical reactions and the law of mass action between metabolites; meanwhile, the metabolic flux distribution used herein consists of all the metabolic fluxes wherein each metabolic flux is assigned to each biochemical reaction.

In the first step of the determination method, a stoichiometric matrix is created based on the biochemical reaction formulas of a substrate through a desired substance product.

The biochemical reactions refer to a process in which intracellular metabolites are converted by enzymatic reactions in the cell, and which have been compiled in various databases according to organism type. For example, Kyoto Encyclopedia of Genes and Genomes (KEGG, www.genome.ad.jp/kegg/) can be accessed for reference.

The substrate is a substance usually used by the cell as a carbon source, and examples thereof include glucose, sucrose, fructose and so forth.

The substance product includes not only a single kind of metabolite, but also an aggregate of metabolites, such as biomass (cell body). Substance production is usually evaluated as a production rate of a substance. In particular, when the desired substance is a biomass, it is evaluated as biomass yield. The biomass yield represents efficiency of conversion from substrates such as glucose into cell components such as protein, carbohydrate, nucleic acid or lipid.

The stoichiometric matrix is a matrix usually used in a metabolic flux analysis, and can be created by listing formulas of biochemical reactions of a substrate through a desired product substance by typical methods used in a metabolic flux analysis. Such methods, assuming a quasi-steady state of an intracellular metabolic intermediate, are generally known (Savinell, J. M. and Palsson, B. O. J., Theor. Biol., 154:421-454, 1992; Vallino, J. J. and Stephanopoulos, G., Biotechnol. Bioeng., 41:633-646, 1993). When reaction formulas are listed, reaction pathways may be simplified by assuming a series of reactions without branching as one reaction, or assuming metabolites converted by a reaction at a high metabolic rate before and after the reaction as one metabolite and so forth. When the substance product is biomass, a stoichiometric matrix can be described by listing biochemical reactions which lead to cell components.

In the second step of the determination method, the same number of independent metabolic fluxes as the degree of freedom of the aforementioned stoichiometric matrix are selected as free fluxes, from all metabolic fluxes.

Independent fluxes are a set of fluxes that should be specified to uniquely define flux in the metabolism network system as defined by a stoichiometric equation.

The method for setting free fluxes is not particularly limited so long as the same number of independent metabolic fluxes as the degree of freedom of the system to be analyzed can be selected. Although the independence of arbitrarily selected fluxes may be confirmed, the SIMS matrix (steady-state internal metabolic stoichiometric matrix) proposed by Reder can also be used (Reder, C. J., Theor. Biol., 135:175-201, 1988). In this method, specific groups of metabolic fluxes in the same number as the degree of freedom of the aforementioned stoichiometric matrix are determined among metabolic flux groups determined based on the aforementioned biochemical reaction formulas, and a metabolic flux is selected as a free flux from each determined metabolic flux group. Determining specific groups among the flux groups ensures that any flux in a group can be changed without affecting the flux in other groups. Therefore, it becomes possible to select one flux from each group as an independent free flux. When a free flux is selected from a flux group, a flux close to a branching point is preferably selected.

In the third step of the determination method, random combinations of free fluxes in a number sufficient for a statistical analysis are created, and a metabolic flux distribution is calculated from each created combination based on the aforementioned stoichiometric matrix.

Random combinations of free fluxes can be created by giving random values to the free fluxes selected in the previous step to create a dataset of combinations of different flux distributions. The method for giving random values to the free fluxes is not particularly limited so long as a method which generates combinations of free fluxes within a specific border is chosen. Said specific border is set to give biologically feasible values in later calculations. If the number of free fluxes is the same as the degree of freedom of the specified stoichiometric matrix, a unique metabolic flux distribution can be solved. For the solution, a matrix operation using an inverse matrix is commonly performed, and all fluxes are preferably normalized into, for example, certain amounts of substrate. When the substrate is glucose, all flux values can be represented, for example, with values per 10 mmol of glucose uptake. The solutions of metabolic flux distributions obtained from random free flux values as described above must be biologically significant. That is, all fluxes of non-reversible reactions must be 0 or more, and biomass forming fluxes must be 0 or more. To obtain combinations of more desirable free fluxes, conditions based on theoretical and/or empirical knowledge in substance production using cells can also be added. The number of combinations to be created, that is, the number of biologically significant flux distributions to be calculated, is not particularly limited so long as it is sufficient for a statistical analysis. Three or five values are usually used for one free flux. Therefore, when there are n free fluxes, there are about to the n-th power of the number of the values for one free flux of combinations. For example, when three values are used for one free flux, there are 3 to the n-th power ($3^n$) of combinations. That is, about 2,200 combinations can be used for seven free fluxes (n=7). Alternatively, since the number of values for each free flux in the dataset of biologically significant flux distributions can change depending on selected free fluxes or additional conditions, the number of combinations that may be used is about 3 to about to the n-th power ($3^n$), or to about 5 to about the n-th power ($5^n$) in total for n of free fluxes. To obtain solutions of biologically significant flux distributions in such a number, it is typical to start from combinations of random free fluxes using 6 to 10 values for one free flux, that is, combinations of free fluxes of six to the n-th power ($6^n$) or 10 to n-th power ($10^n$).

In the fourth step of the determination method, a regression equation including a minimum number of free fluxes that show a correlation with substance production is obtained from the metabolic flux distributions (dataset of metabolic flux distributions) by a multivariate statistical analysis.

By performing a multivariate statistical analysis for the dataset of flux distributions calculated from random combinations of the free fluxes obtained in the previous step, a regression equation including a minimum number of free fluxes that shows a correlation with substance production can be obtained. The multivariate statistical analysis (including multivariate non-linear regression analysis and multivariate linear regression analysis) can be performed by using any technique so long as a technique is chosen which can examine correlations of free flux combinations with substance production. However, a multivariate linear regression analysis is useful. This method is described in, for example, Kachigan, S. K., Chapter 4, Regression Analysis in Multivariate Statistical Analysis 2nd Ed., Radius Press, New York, pp. 160-193.

The expression "shows a correlation with substance production" means that the coefficient of determination is significantly large, and "being significantly large" usually means that the coefficient of determination $R^2$ is 0.8 or higher, preferably 0.9 or higher.

A regression equation, including a minimum number of free fluxes (terms) that shows a correlation with substance production, may be obtained by successively changing the number of terms to obtain a regression equation. Such an equation that shows the largest coefficient of determination, including each number of terms, and enables selecting a regression equation including a minimum number of terms that shows a significantly large coefficient of determination. Alternatively, a regression equation may be obtained with the total terms except for one term to examine the degree of decrease in the coefficient of determination due to the exclusion of the term; the same procedure may be repeated with terms except for the term showing decrease in a small degree of the coefficient of determination, as the total terms; and when a regression equation that shows a correlation with substance production can no longer be obtained, the regression equation obtained immediately therebefore may be selected.

Although these mathematical procedures can be individually programmed, they can be readily performed by using commercially available mathematical computation programs such as MatLab® (trade name, MathWorks) and Mathematica® (trade name, Wolfram Research).

In the fifth step of the determination method, a metabolic flux affecting substance production is determined based on coefficients in the obtained regression equation.

Contributions of free fluxes to substance production using cells such as microorganisms, in particular, biomass yield or product substance yield, which are important in substance production, can be determined by utilizing the regression equation obtained in the previous step. That is, free fluxes that appear in the regression equation can be determined as those affecting substance production. Furthermore, since coefficients in the regression equation represent the magnitude of contribution, free fluxes having a substantially large coefficient (when fluxes are normalized, free fluxes having a large absolute value of relative coefficient) can be determined as metabolic fluxes that greatly affect substance production.

The determination method of the present invention can provide information which is important for improving bacterial strains, i.e., which free flux greatly influences the production of a target substance, and whether a free flux has a positive or negative effect on the production of a target substance. A flux that needs to be changed to favorably affect the yield and productivity of a target product can also be predicted.

For example, as shown in the examples described herein, it can be expected that bacterial strains with an improved lysine-producing ability can be created by enhancing activity of phosphoenolpyruvate carboxylase in lysine production using *Escherichia coli*. International Publication No. WO01/53459 discloses an example of improvement of lysine production by enhancing phosphoenolpyruvate carboxylase activity. Therefore, it has been verified that a bacterial strain having a substance-producing ability can be created based on the determination method.

<3> Production Method for Producing L-Lysine or L-Threonine

The method of the present invention is a method for producing L-lysine or L-threonine, which method comprises the steps of cultivating the bacterium having an ability to produce L-lysine or L-threonine in a medium, to cause accumulation of L-lysine or L-threonine in the medium or cells of the bacterium, and to collect L-lysine or L-threonine from the medium or the cells.

The culture medium used in the present invention may be a medium typically used for fermentation production of L-lysine or L-threonine using a microorganism. An ordinary medium including a carbon source, a nitrogen source, inorganic ions and the other organic components, if necessary, may be used. As the carbon source, various saccharides such as glucose, sucrose, lactose, galactose, fructose, and starch hydrolysate, various alcohols such as glycerol and sorbitol, and various organic acids such as fumaric acid, citric acid and succinic acid may be used. As the nitrogen source, various inorganic ammonium salts such as ammonium sulfate, ammonium chloride and ammonium phosphate, organic nitrogen such as soybean hydrolysate, ammonia gas and aqueous ammonia and the like may be used. As a trace organic nutrient, it is desirable to add required substances such as vitamin $B_1$, homoserine, or yeast extract and the like. In addition, a trace amount of potassium phosphate, magnesium sulfate, iron ion, manganese ion may be added. The medium used for culture may be either a synthetic medium or a natural medium, so long as the medium includes a carbon source and a nitrogen source and inorganic ions and, if necessary, trace organic nutrients.

The cultivation is preferably performed under aerobic conditions for one to seven days at a temperature of 24 to 37° C., and a pH of 5 to 9. The pH of the culture can be adjusted with an inorganic or organic acid or alkaline substance, for example, ammonia gas and the like. The collection L-lysine or L-threonine from the culture medium may be performed by usual methods, such as an ion-exchange resin method, precipitation, and the other known methods, and combinations thereof. When L-lysine or L-threonine accumulates in cells, L-lysine or L-threonine may be collected by an ion-exchange resin method or the like from a supernatant obtained by disrupting the cells by ultrasonic or the like, and removing cell debris by centrifugation.

EXAMPLES

The present invention is further described in detail by referent to examples.

Example 1

Determination of Metabolic Flux with Respect to L-lysine (1) Creation of Stoichiometric Matrix A stoichiometric equation for calculating a metabolic flux was constructed by assuming a quasi-steady state of intracellular metabolic intermediates (Savinell, J. M. and Palsson, B. O. J., Theor. Biol., 154:421-454, 1992; Vallino, J. J. and Stephanopoulos, G., Biotechnol. Bioeng., 41:633-646, 1993). The reaction formulas included in this model are shown in Table 2. Descriptions of the abbreviations used in the present invention are listed in Table 1. Some reactions without branching were consolidated to simplify the formulas. Since the pentose phosphate pathway is complicated, it was represented by two formulas. Reported data was used for the component ratio of biomass (Neidhardt, F. C. et al., Physiology of the Bacterial Cell., Sinauer Associates, Massachusetts, 1990) and the biomass was represented by using the reaction formula [68]. The degree of freedom of the stoichiometric matrix in this model was 7.

TABLE 1

| | |
|---|---|
| 3PG | 3-Phospho-D-glyceric acid |
| AcCoA | Acetyl coenzyme A |
| AcOH | Acetic acid |
| aIVA | A-Keto-isovaleric acid |
| aKG | 2-Oxoglutaric acid |
| Ala | Alanine |
| ALC | Acetohydroxy acid |
| Arg | Arginine |
| ASA | Aspartic acid semialdehyde |
| Asn | Asparagine |
| Asp | Aspartic acid |
| CHR | Chorismic acid |
| Cit | Citric acid |
| CO2 | Carbon dioxide |
| CoA | Coenzyme A |
| Cys | Cysteine |
| DDP | Dihydrodipicolinic acid |
| E4P | Erythrose-4-phosphate |
| F6P | Fructose-6-phosphate |
| FBP | Fructose bisphosphate |
| Form | Formic acid |
| Fum | Fumaric acid |
| G6P | Glucose-6-phosphate |
| GAP | Glyceraldehyde phosphate |
| Glc | Glucose |
| Gln | Glutamine |
| Glu | Glutamic acid |
| Gly | Glycine |
| Glyox | Glyoxylic acid |
| His | Histidine |
| Hse | Homoserine |
| Ile | Isoleucine |
| Ind | Indole glycerol phosphate |
| Isocit | Isocitric acid |
| Leu | Leucine |
| Lys | Lysine |
| Lysext | Lysine product (extracellular) |
| Mal | Malic acid |
| Met | Methionine |
| mDAP | meso-Diaminopimelic acid |
| mTHF | Methyl tetrahydrofolate |
| NH3 | Ammonia |
| OAA | Oxaloacetatic acid |
| PEP | Phosphoenolpyruvic acid |
| Phe | Phenylalanine |
| PPA | Prephenic acid |
| Pro | Proline |
| PRPP | Phophoribosyl pyrophosphate |
| Pyr | Pyruvic acid |
| R5P | Ribose-5-phosphate |
| Ribu5P | Ribulose-5-phosphate |
| SDAP | N-Succinyl-L-2,6-diaminoheptanedioate |
| SKA | Shikimic acid |
| Sed7P | D-Sedoheptulose-7-phosphate |
| Ser | Serine |
| Suc | Succinic acid |
| SucCoA | Succinyl coenzyme A |
| THDP | Tetrahydropicolinic acid |
| THF | Tetrahydrofolic acid |
| Thr | Threonine |
| Trp | Tryptophan |
| Tyr | Tyrosine |
| Val | Valine |
| X5P | Xylulose-5-phosphate |

TABLE 2

List of used reaction formulas. Reversible reactions are marked with r.

- [1]     Glc + PEP --> G6P + Pyr
- [2]     G6P + 2NADP --> Ribu5P + 2NADPH + CO2
- [3] r   Ribu5P --> R5P
- [4] r   Ribu5P --> X5P
- [5] r   X5P + R5P --> Sed7P + GAP
- [6] r   Sed7P + GAP --> E4P + F6P
- [7] r   X5P + E4P --> F6P + GAP
- [8] r   G6P --> F6P
- [9] r   F6P + ATP --> FBP + ADP
- [10] r  FBP --> 2GAP
- [11] r  GAP + NAD + ADP --> 3PG + NADH + ATP
- [12] r  3PG --> PEP
- [13]    PEP + ADP --> Pyr + ATP
- [14]    Pyr + NAD + CoA --> AcCoA + NADH + CO2
- [15]    PEP + CO2 --> OAA
- [16]    AcCoA + ADP --> AcOH + ATP + CoA
- [17]    AcCoA + OAA --> Cit + CoA
- [18] r  Cit --> Isocit
- [19] r  Isocit + NADP --> aKG + NADPH + CO2
- [20]    aKG + NADPH + NH3 --> Glu + NADP
- [21]    aKG + NAD + CoA --> SucCoA + NADH + CO2
- [22] r  SucCoA + ADP --> Suc + ATP + CoA
- [23] r  Suc + FAD --> Fum + FADH
- [24] r  Fum --> Mal
- [25] r  Mal + NAD --> OAA + NADH
- [26]    OAA + Glu --> Asp + aKG
- [27]    Asp + ATP + NADPH --> ASA + ADP + NADP
- [28]    ASA + Pyr --> DDP
- [29]    DDP + NADPH --> THDP + NADP
- [30]    THDP + SucCoA + Glu --> SDAP + aKG + CoA
- [31]    SDAP --> mDAP + Suc
- [32]    mDAP --> Lys + CO2
- [33] r  Glu + ATP + NH3 --> Gln + ADP
- [34]    Glu + 2NADPH + ATP --> Pro + 2NADP + ADP
- [35]    Glu + 5ATP + NADPH + Gln + Asp + AcCoA + CO2 --> Arg + 5ADP + NADP + aKG + Fum
- [36]    ASA + NADPH --> Hse + NADP
- [37]    Hse + SucCoA + Cys + mTHF --> Met + Suc + CoA + THF + Pyr + NH3
- [38]    Hse + ATP --> Thr + ADP
- [39]    Thr + Glu + NADPH + Pyr --> Ile + aKG + NADP + NH3 + CO2
- [40] r  3PG --> Ser
- [41] r  Ser + THF --> Gly + mTHF
- [42] r  PEP + E4P + NADPH --> SKA + NADP
- [43]    CHR --> PPA
- [44]    PPA + NAD + Glu --> Tyr + NADH + CO2 + Akg
- [45]    PPA + Glu --> Phe + CO2 + aKG
- [46]    CHR + R5P + 2ATP + Gln --> Ind + Glu + Pyr + CO2 + GAP + 2ADP
- [47]    2Pyr --> ALC
- [48]    aIVA + Glu --> Val + aKG
- [49]    Val + Pyr --> ALA + aIVA
- [50]    aIVA + AcCoA + NAD + Glu --> Leu + NADH + CO2 + aKG + CoA
- [51]    PRPP + ATP + Gln + Glu + 2NAD --> His + ADP + Glu + aKG + 2NADH
- [52]    Ser + AcCoA + H2S --> Cys + AcOH
- [53]    SKA + PEP + ATP --> CHR + ADP
- [54]    Ind + Ser --> Trp
- [55]    ALC + NADPH --> aIVA + NADP + CO2
- [56] r  NADH --> NADPH
- [57]    2NADH + O2 + 2ADP --> 2ATP + 2NAD
- [58]    2FADH + O2 + ADP --> ATP + 2FAD
- [59] r  Asp + 2 ATP + NH3 --> Asn + 2 ADP
- [60]    Isocit --> Glyox + Succ
- [61]    AcCoA + Glyox --> Mal + CoA
- [62]    Mal + NAD --> Pyr + CO2 + NADH
- [63] r  R5P + 2 ATP --> PRPP + 2 ADP
- [64]    mTHF + NADP --> NADPH + THF + Form
- [65]    NAD + Gly + THF --> mTHF + NADH + CO2 + NH3
- [66]    ATP --> ADP
- [67]    Lys --> Lysext
- [68]    Biomass synthesis (described below)
    RNA (21.33%)
    3.47 PRPP + 5.02 Gln + −5.02 Glu + 3.08 Gly + 6.17 Asp + 32.41 ATP + −32.41 ADP + 6.17
    mTHF + −6.17 THF + 3.09 NAD + −3.09 NADH + 6.17 NADP + −6.17 NADPH + 1.16
    CO2 + −3.47 Fum + −3.86 NH3
    DNA (3.23%)
    3.37 PRPP + 4.88 Gln + −4.88 Glu + 3 Gly + 6 Asp + 31.5 ATP + −31.5 ADP + 7.12
    mTHF + −7.12 THF + 3 NAD + −3 NADH + 3.75 NADP + −3.75 NADPH + 1.12 CO2 + −3.37
    Fum + −3.75 NH3
    Phospholipid (9.47%)

TABLE 2-continued

List of used reaction formulas. Reversible reactions are marked with r.

20.8 AcCoA + −20.8 CoA + 1.95 GAP + 0.65 Ser + 44.2 ATP + −44.2 ADP + 38.35 NADH + −38.35 NAD + −0.65 CO2
Peptidoglycan (2.60%)
1.94 F6P + 1.94 AcCoA + −1.94 CoA + 1.94 Gln + −1.94 Glu + 2.91 Ala + 0.97 PEP + 0.97 Lys + 6.97 ATP + −6.97 ADP + 0.97 NADPH + −0.97 NADP + −0.97 CO2
Lipopolysaccharide (3.54%)
0.91 R5P + 0.91 F6P + 0.91 PEP + 15.47 AcCoA + −0.91 AcOH + −0.91 Glu + 0.91 Gln + 32.76 ATP + 12.74 NADH
Protein (57.23%)
0.77 Gly + 0.96 Ala + 0.67 Val + 0.85 Leu + 0.44 Ile + 0.44 Ser + 0.48 Thr + 0.30 Phe + 0.26 Tyr + 0.01 Trp + 0.15 Cys + 0.22 Met + 0.54 Lys + 0.46 Arg + 0.16 His + 0.46 Asp + 0.52 Glu + 0.46 Asn + 0.52 Gln + 0.34 Pro
Glycogen (2.60%)
F6P + ATP (2) Selection of Free Fluxes and Creation of Random Combinations of Them Specific flux groups were determined according to the method of Reder (Reder, C. J., Theor. Biol., 135:175-201, 1988). A flux close to a branch point was selected from each group. Seven selected free fluxes are shown in Table 3. A unique solution for a flux balance can be obtained by specifying these 7 fluxes.

TABLE 3

List of free fluxes for obtaining random flux distribution

| Reaction number | Enzyme name or reaction pathway name |
|---|---|
| 2 | Glucose-6-phosphate dehydrogenase |
| 15 | PEP carboxylase |
| 16 | Acetic acid secretion |
| 60 | Isocitrate lyase (glyoxylate cycle) |
| 62 | Malic enzyme |
| 64 | Formic acid secretion |
| 66 | ATPase |

From the about 300,000 combinations of values for 7 random free fluxes, those infringing any limitation concerning reverse reactivity and those showing values for both lysine and biomass not exceeding the threshold levels set at 20% of each maximum value were excluded. As a result, a dataset was created of 5000 metabolic flux distributions in a biologically significant specific region. The results were represented by values based on 10 mmol glucose uptake, and a matrix was created with 5000 rows corresponding to the random flux distributions and 68 columns each of which corresponds to a reaction flux.

(3) Correlation Analysis by Multivariate Analysis and Determination of Metabolic Fluxes Affecting Substance Production Multivariate linear regression of a condensed matrix including Z-scores of only columns corresponding to the 7 free fluxes was performed. The stepwise regression function of the MatLab statistical toolbox was used for multivariate linear regression. With this technique, biomass or lysine production can be derived with a linear function of 7 free fluxes. Identification of these 7 fluxes results in unique definition of the state of the system. Therefore, if all the 7 terms are used as parameters, the correlation coefficient becomes 1, indicating a complete fit. However, it is usually possible to obtain a relatively favorable fit with a fewer number of terms than in the equation. To try various combinations of terms, an equation showing the best fit for each number of contained terms was selected by using the stepwise function of the MatLab program. As for the biomass yield, a fit of $R^2=0.980$ was obtained with only 4 terms, isocitrate lyase (ICL), malic enzyme (MEZ), PEP carboxylase (PEPC) and ATPase. When the number of terms is further decreased, the $R^2$ value is markedly decreased, and any reasonable fit could not be obtained. When reaction fluxes are normalized to a value per 10 mmol glucose and used as the input, an accurate equation was represented as follows:

Biomass yield=1.552−0.194(ICL)+0.184(MEZ)−0.194(PEPC)−0.011(ATPase)  Equation 1)

The lysine yield could be fit with a model including the same 4 parameters, and the result of $R^2=0.997$ was obtained. Further, even when the term for ATPase was excluded, $R^2$ decreased only to 0.856, and the fit was still favorable. Therefore, the following 3 parameters were used for the model of lysine.

Lysine yield=−1.694+1.176(ICL)−1.095(MEZ)+1.162(PEPC)  Equation 2)

Finally, the total carbon yield (C atoms) defined with the total number of carbon atoms directing to biomass and lysine could be fit with $R^2=0.956$ by using only the term for ATPase with the following equation.

$C$ atoms=34.3−0.314(ATPase)  Equation 3)

Figure 2:
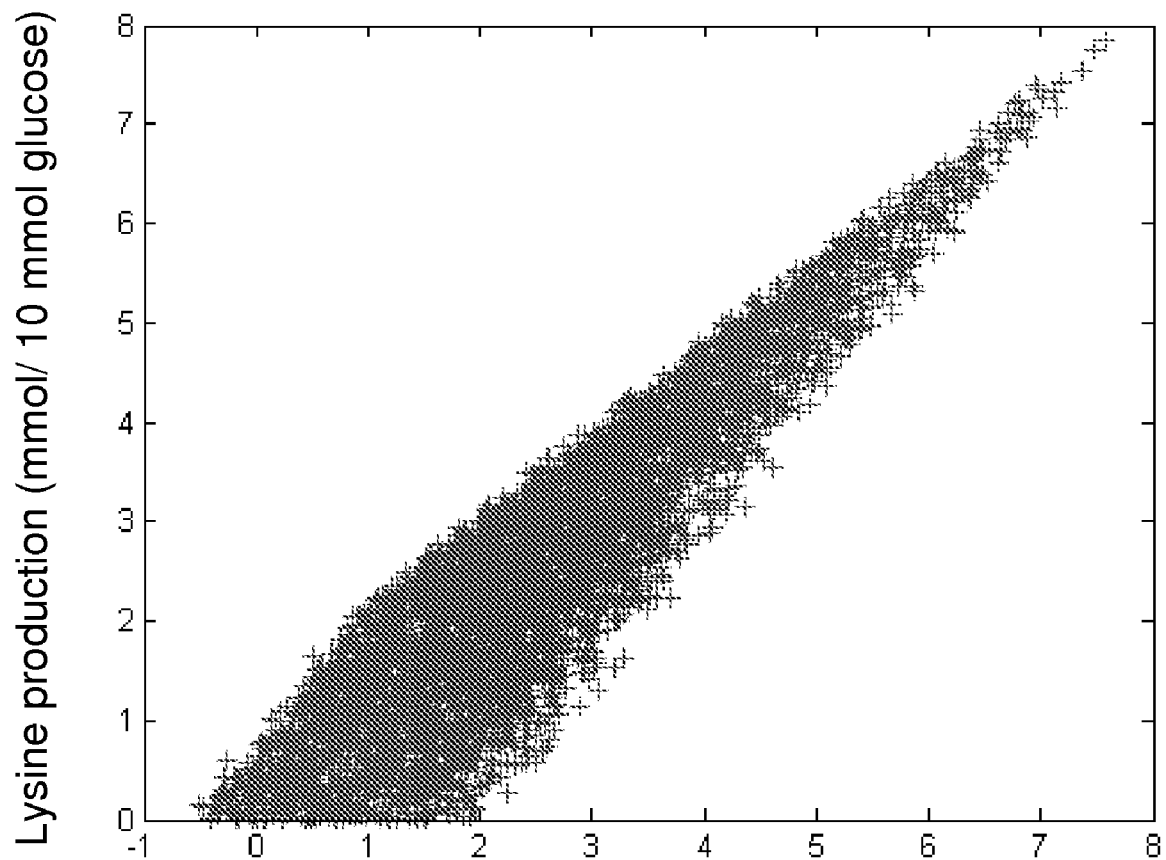
FIG. 2 is a plot showing lysine production as a function of values in equation 2 for a dataset of 5000 random flux distributions. The input value is a flux in mmol/hr based on 10 mmol/hr glucose flux.
Figure 3:
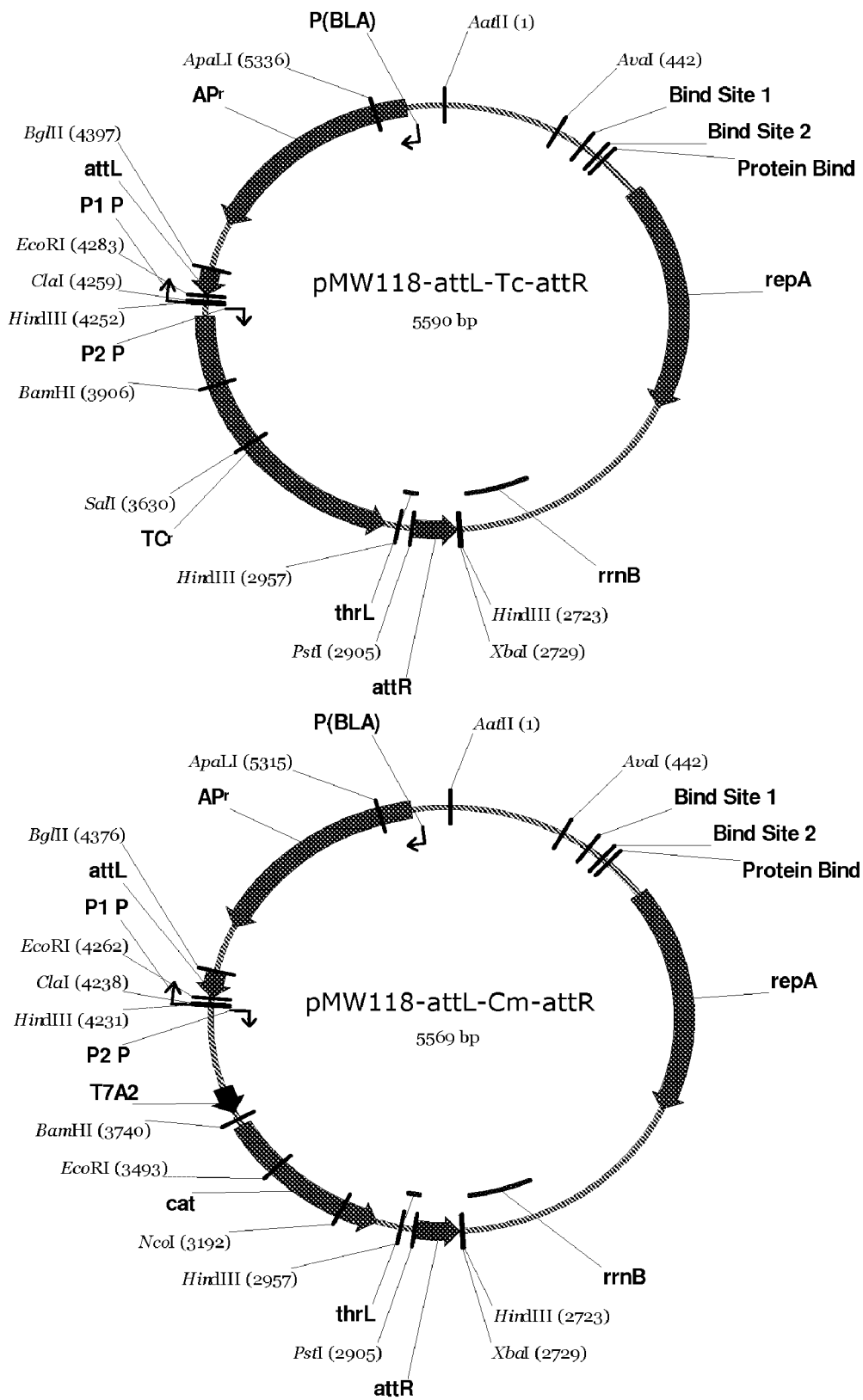
FIG. 3 shows the structures of pMW118-attL-Tc-attR and pMW118-attL-Cm-attR.
Figure 4:
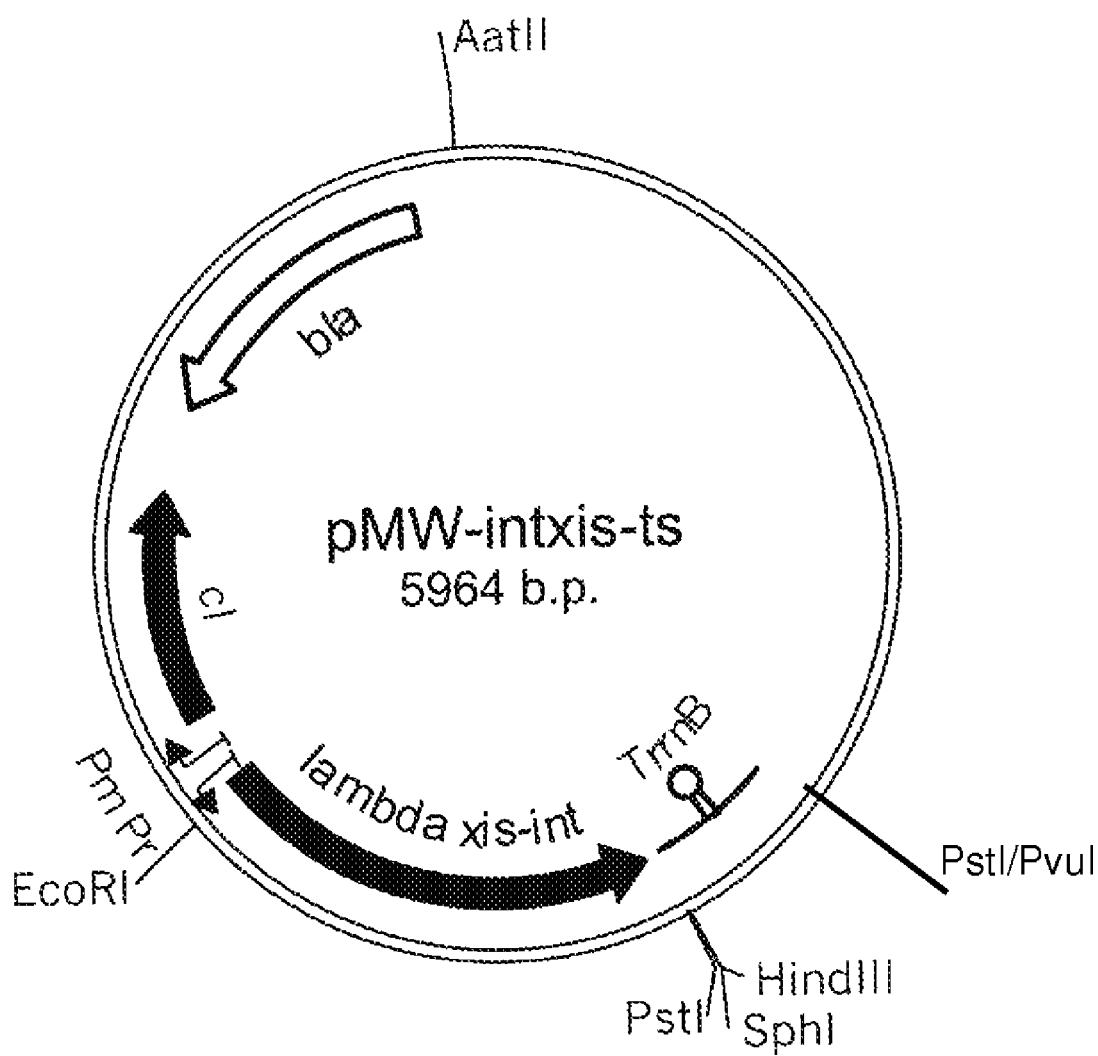
FIG. 4 shows the structure of pMW-intxis-ts.

These results revealed that the biomass yield positively correlated with the flux of malic enzyme, and that lysine production positively correlated with the fluxes of PEP carboxylase and isocitrate lyase (glyoxylate cycle). Usefulness of this regression analysis can be shown in FIGS. 1 and 2. When the fluxes of isocitrate lyase and malic enzyme are separately considered, no correlation with lysine production is observed as shown in FIG. 1, (a) and (b). However, when these fluxes are considered as a part of the regression equation 2), a correlation as shown in FIG. 2 can be observed, and the effect becomes clear. Thus, an invisible relationship between metabolic fluxes can be revealed with this technique. Yield of a target product can be improved by enhancing an activity responsible for a flux showing a positive correlation, and attenuating an activity responsible for a flux showing a negative correlation. That is, from this result, a guideline for improving bacterial strains could be obtained, and enhancement of the PEP carboxylase or isocitrate lyase activity or attenuation of the activity of malic enzyme showing a negative correlation is effective for lysine production. In fact, an example of creation of a bacterial strain showing an improved lysine producing ability by enhancing activity of PEP carboxylase in lysine production using *Escherichia coli* was disclosed in International Publication No. WO01/53459, and thus usefulness of the present invention has been supported.

Example 2

Determination of Metabolic Flux with Respect to L-threonine

By the same method as in Example 1, an equation showing the best fit for each number of contained terms was selected with respect to L-threonine. As for the biomass yield, a fit of $R^2=0.986$ was obtained with only 4 terms, isocitrate lyase (ICL), malic enzyme (MEZ), PEP carboxylase (PEPC) and ATPase.

Biomass yield=1.260−0.101(ICL)+0.093(MEZ)− 0.101(PEPC)−0.009(ATPase)        Equation 4

The threonine yield could be fit with a model including the same 3 parameters, and the result of $R^2=0.937$ was obtained.

Threonine yield=−1.432+1.090(ICL)−1.080(MEZ)+ 1.087(PEPC)        Equation 5

These results revealed that the biomass yield positively correlated with the flux of malic enzyme, and that threonine production positively correlated with the fluxes of PEP carboxylase and isocitrate lyase (glyoxylate cycle). Therefore, with respect to threonine production, a guideline for improving bacterial strains could be also obtained, and enhancement of the PEP carboxylase or isocitrate lyase activity or attenuation of the activity of malic enzyme showing a negative correlation is effective for lysine production.

Example 3

Construction of Malic Enzyme-Deficient L-Lysine-Producing Bacterium

Strain WC196 was used as the L-lysine-producing strain of *Escherichia coli* which is resistant to AEC (S-(2-aminoethyl)cysteine) (International Publication No. WO 96/17930).

The malic enzyme from *Escherichia coli* includes one using NAD as coenzyme (EC 1.1.1.38) and one using NADP as coenzyme (EC 1.1.1.40). These enzymes are encoded by the sfcA and b2463 genes, respectively.

The sfcA and b2463 genes are deleted by a combination of the "red-driven integration" method, which was originally developed by Datsenko and Wanner (Proc. Natl. Acad. Sci. USA, 2000, 97, 6640-6645), and the excision system method, derived from lambda phage (J. Bacteriol. 2002 September; 184(18): 5200-3. Interactions between integrase and excisionase in the phage lambda excisive nucleoprotein complex. Cho EH, Gumport RI, Gardner JF.). According to the red-driven integration method, a gene-disrupted strain can be constructed in one step by using PCR product obtained by using synthetic oligonucleotide primers designed to comprise a part of a targeted gene at its 5' terminal and a part of an antibiotic resistance gene at its 3' terminal. Furthermore, the integrated antibiotic resistance gene can be removed by further combining the excision system derived from lambda phage with the red-driven integration method.

(1) Disruption of sfcA Gene

As a PCR template, plasmid pMW118-attL-Cm-attR (its preparation is described below) was used. pMW118-attL-Cm-attR is a plasmid obtained by inserting attL and attR genes which are the attachment sites of lambda phage, and a cat gene which is the antibiotic resistance gene to pMW118 (TaKaRa Bio). The genes are inserted in the order of attL-cat-attR. The attL sequence is shown in SEQ ID NO: 11 and the attR sequence is shown in SEQ ID NO: 12.

PCR was performed by using primers shown in SEQ ID NOS: 1 and 2, and having sequences corresponding to their 3' terminus ends of attL and attR and sequences corresponding to parts of the sfcA gene at their 5' terminus, respectively.

The amplified PCR product was purified on an agarose gel and introduced into *Escherichia coli* WC196 containing plasmid pKD46 showing temperature-sensitive replication, by eletroporation. pKD46 (Proc. Natl. Acad. Sci. USA, 2000, 97, 6640-6645) includes a 2,154 nt DNA fragment of lambda phage (GenBank/EMBL accession No. J02459, 31088-33241) containing genes (γ, β, and exo genes) encoding Red recombinase of the λ Red homologous recombination system under the control of the arabinose-inducible $P_{araB}$ promoter. pKD46 is necessary for integrating the PCR product into the chromosome of the strain WC196.

Competent cells for electroporation were prepared as follows. The *Escherichia coli* WC196 which was cultured overnight at 30° C. in LB medium containing 100 mg/l ampicillin, was diluted 100 times with 5 mL SOB medium (Sambrook, J. et al., "Molecular Cloning A Laboratory Manual, Second Edition", Cold Spring Harbor Laboratory Press (1989)) containing amplicillin (50 mg/l) and L-arabinose (1 mM). The diluted product was cultured at 30° C. under aeration until the $OD_{600}$ became about 0.6, and then concentrated 100 times. Cells were washed three times with 10% glycerol to prepare cells ready for electroporation. Electroporation was performed with 70 μl competent cells and about 100 ng of the PCR product. 1 ml SOC medium (Sambrook, J. et al., "Molecular Cloning A Laboratory Manual, Second Edition", Cold Spring Harbor Laboratory Press (1989)) was added to the cells subjected to electroporation. The cells were cultured at 37° C. for 2.5 hours, and then plate-cultured on L-agar medium containing 25 mg/l Cm (chloramphenicol) at 37° C. to select a Cm-resistant recombinant. Then, to lose the plasmid pKD46, cells were subcultured twice at 42° C. on Cm-containing L-agar medium. The obtained colonies are tested for ampicillin resistance. An ampicillin-sensitive strain without pKD46 is obtained.

The deletion of the sfcA gene of the mutant identified by the chloramphenicol resistance gene was confirmed by PCR. The resultant sfcA-deficient strain was designated as WC196ΔsfcA::att-cat.

To eliminate the att-cat gene which had been integrated into the sfcA gene, a helper plasmid pMW-intxis-ts (its preparation is described below) was used. pMW-intxis-ts harbors a gene encoding integrase (Int) (SEQ ID NO: 13) and a gene encoding excisionase (Xis) (SEQ ID NO: 15) of lambda phage and shows temperature-sensitive replication. By introduction of the pMW-intxis-ts, recombination occurs due to the recognition of attL (SEQ ID NO: 11) and attR (SEQ ID NO: 12) on the chromosome, and the antibiotic resistance gene between attL and attR is excised, resulting in a structure whereby only attL or attR sequence remains on chromosome.

Competent cells of the strain WC196ΔsfcA::att-cat were prepared according to an ordinary method, transformed with the helper plasmid pMW-intxis-ts, and plate-cultured at 30° C. on L-agar medium containing 50 mg/l ampicillin to select an ampicillin-resistant strain.

To lose the plasmid pMW-intxis-ts, cells were subcultured twice at 42° C. on L-agar medium. The obtained colonies are tested for ampicillin resistance and chloramphenicol resistance. An ampicillin- and chloramphenicol-sensitive strain without att-cat and pMW-intxis-ts is obtained. This strain was designated as WC196ΔsfcA.

(2) Disruption of b2463 Gene

Deletion of the b2463 gene in strains WC196 and WC196ΔsfcA was performed according to the method of (1) except primers of SEQ ID NOS: 3 and 4 were used as primers for disrupting b2463. Thus, the strains WC196Δb2463 and WC196ΔsfcAΔb2463 were obtained. The obtained strain WC196ΔsfcAΔb2463 was designated as WC196Δmez.

(3) Preparation of PCR Template and Helper Plasmid

The PCR template pMW118-attL-Cm-attR and the helper plasmid pMW-intxis-ts were prepared as follows:

(3-1) pMW118-attL-Cm-attR

For construction of the plasmid pMW118-attL-Cm-attR, the pMW118-attL-Tc-attR was used to start. Four DNA fragments were ligated:
1) BglII-EcoRI—the DNA fragment (120 bp) (SEQ ID NO: 11) carrying attL which was obtained by PCR amplification of the corresponding sequence of *E. coli* W3350 (contained λ prophage) chromosome using the oligonucleotides P1 and P2 (SEQ ID NOS: 17 and 18) as primers (these primers contained the subsidiary recognition sites for BglII and EcoRI endonucleases);
2) PstI-HindIII—the DNA fragment (182 bp) carrying attR (SEQ ID NO: 12) which was obtained by PCR amplification of the corresponding sequence of *E. coli* W3350 (contained λ prophage) chromosome using the oligonucleotides P3 and P4 (SEQ ID NOS: 19 and 20) as primers (these primers contained the subsidiary recognition sites for PstI and HindIII endonucleases);
3) the large (3916 bp) BglII-HindIII fragment of pMW118-ter_rrnB. pMW118-ter_rrnB was obtained by ligation of three DNA fragments:
   the large (2359 bp) fragment carrying the AatII-EcoRIpol fragment of the pMW118, pMW118 was digested with EcoRI restriction endonuclease, treated with Klenow fragment of DNA polymerase I and then was digested with AatII restriction endonuclease;
   the small fragment (1194 bp) AatII-BglII of pUC19 carrying the bla gene for ampicillin resistance ($Ap^R$) was obtained by PCR amplification of the corresponding sequence of pUC19 plasmid using oligonucleotides P5 and P6 (SEQ ID NOS: 21 and 22) as primers (these primers contained the subsidiary recognition sites for AatII and BglII endonucleases);
   the small fragment (363 bp) BglII-PstIpol of the transcription terminator ter_rrnB was obtained by PCR amplification of the corresponding region of *E. coli* MG1655 chromosome using the oligonucleotides P7 and P8 (SEQ ID NOS: 23 and 24) as primers (these primers contained the subsidiary recognition sites for BglII and PstI endonucleases);
4) the small fragment (1388 bp) EcoRI-PstI (SEQ ID NO: 29) of pML-Tc-ter_thrL including the gene for tetracycline resistance and the transcription terminator ter_thrL, the pML-Tc-ter_thrL was obtained in the following way:
   the pML-MSC (2001 #5) was digested with XbaI and BamHI restriction endonucleases and then the large (3342 bp) fragment was ligated with the fragment (68 bp) XbaI-BamHI carrying terminator ter_thrL which was obtained by PCR amplification of the corresponding region of *E. coli* MG1655 chromosome using the oligonucleotides P9 and P10 (SEQ ID NOS: 25 and 26) as primers (these primers contained the subsidiary recognition sites for XbaI and BamHI endonucleases), the product of this reaction was the plasmid pML-ter_thrL;
   then the pML-ter_thrL was digested with KpnI and XbaI restriction endonucleases then treated with Klenow fragment of DNA polymerase I and then was ligated with the small (1317 bp) EcoRI-Van91I fragment of pBR322 including the gene for tetracycline resistance (pBR322 was digested with EcoRI and Van91I restriction endonucleases then which have been treated with Klenow fragment of DNA polymerase I), the product of this reaction was the plasmid pML-Tc-ter_thrL; so pMW118-attL-Tc-attR was obtained.

pMW118-attL-Cm-attR was constructed by ligation of large (4413 bp) BamHI-XbaI fragment of pMW 118-attL-Tc-attR and BglII-XbaI the artificial DNA fragment (1162 bp) including the promoter $P_{A2}$ (the early promoter of the phage T7), the cat gene for chloramphenicol resistance ($Cm^R$), the transcription terminator ter_thrL and attR. The artificial DNA fragment (SEQ ID NO: 30) was obtained in the following way:
1. the pML-MSC (2001 #5) was digested with KpnI and XbaI restriction endonucleases and ligated with the small (120 bp) KpnI-XbaI fragment which includes the promoter $P_{A2}$ (the early promoter of the phage T7) obtained by PCR amplification of the corresponding region of phage T7 DNA the oligonucleotides P11 and P12 (SEQ ID NOS: 27 and 28) as primers (these primers contained the subsidiary recognition sites for KpnI and XbaI endonucleases), the product of this reaction was the plasmid pML-$P_{A2}$-MCS;
2. then the XbaI site was deleted from the pML-$P_{A2}$-MCS, the product of this reaction was the plasmid pML-$P_{A2}$-MCS(XbaI$^-$);
3. then the small fragment (928 bp) BglII-HindIII of the pML-$P_{A2}$-MCS(XbaI$^-$) including the promoter $P_{A2}$ (the early promoter of the phage T7) and gene cat for chloramphenicol resistance ($Cm^R$) was ligated with the small (234 bp) fragment HindIII-HindIII of pMW118-attL-Tc-attR including the transcription terminator ter_thrL and attR;
4. the required artificial DNA fragment (1156 bp) was obtained by PCR amplification with the ligation reaction mixture using the oligonucleotides P9 and P4 (SEQ ID NOS: 25 and 20) as primers (these primers contained the subsidiary recognition sites for HindIII and XbaI endonucleases).

(3-2) pMW-intxis-ts

Initially, two DNA fragments were amplified using phage λ DNA ("Fermentas") as a template. The first one included the region from nt 37168 to 38046 (SEQ ID NO: 39) and also contained the gene encoding the cI repressor, promoters Prm and Pr, and leader sequence of the cro gene. This fragment was obtained using the P1' and P2' oligonucleotides (SEQ ID NOS: 31 and 32) as primers. The second fragment carried xis-int genes of phage λ and comprised the region from nt 27801 to 29100 (SEQ ID NO: 40). Oligonucleotides P3' and P4' (SEQ ID NOS: 33 and 34) were used as primers for its amplification. All primers contained appropriate endonuclease recognition sites.

The obtained PCR-amplified fragment, carring the cI repressor, was digested with restriction endonuclease ClaI, treated with Klenow fragment of DNA polymerase I, and then digested with EcoRI restriction endonuclease. The second PCR-amplified fragment was digested with EcoRI and PstI restriction endonucleases. Then the pMWPlaclacI-ts plasmid was digested with BglII endonuclease, treated with Klenow fragment of DNA polymerase I and then digested with PstI restriction endonuclease. A vector fragment of pMWPlaclacI-ts was eluted from the agarose gel and ligated with the digested PCR-amplified fragments.

Plasmid pMWPlaclacI-ts is a derivative of pMWPlaclacI which consist of the following parts: 1) BglII-HindIII—artificial DNA fragment including the lacI gene under control of the $P_{lacUV5}$ promoter and RBS of bacteriophage T7 gene 10; 2) AatII-BglII—DNA fragment carrying the gene for ampicillin resistance ($AP^R$) which was obtained by PCR amplification of the corresponding sequence of pUC 19 plasmid using oligonucleotides P5' and P6' (SEQ ID NOS: 35 and 36) as primers (these primers contained the subsidiary recognition sites for AatII and BglII endonucleases); 3) AatII-HindIII—fragment comprising AatII-PvuI fragment of the previously constructed recombinant plasmid—pMW118-ter_rrnB. The later plasmid was constructed in the following fashion: the PstI-HindIII DNA fragment carrying terminator ter_rrnB has been obtained by PCR amplification of the corresponding region of E. coli MG1655 chromosome using the oligonucleotides P7' and P8' (SEQ ID NOS: 37 and 38) containing appropriate endonuclease recognition sites as primers. Before ligation, pMW118 plasmid and ter_rrnB DNA fragment (complement, SEQ ID NO: 41) were restricted with PvuI or PstI endonuclease respectively, treated with Klenow fragment of DNA polymerase I to obtain the blunt ends and then restricted with AatII or HindIII endonuclease. To construct the pMWPlaclacI-ts variant the AatII-EcoRV fragment of the pMWPlaclacI plasmid was substituted by AatII-EcoRV fragment of the plasmid pMAN997 including the loci par, ori and $repA^{ts}$ gene of pSC101 replicon.

Example 4

Construction of Malic Enzyme-Deficient L-Threonine-Producing Bacterium sfcA- and b2463-deficient strains were constructed from strain VKPM B-5318. The strain VKPM B-5318 strain was deposited at Russian National Collection of Industrial Microorganisms (VKPM), GNII Genetika on Nov. 19, 1987 and received an accession number of VKPM B-5318.

A strain which was deficient in one of the malic enzyme (mez) genes (sfcA, b2463) was obtained in the same way as in Example 3 using the "red-driven integration" method. Namely, it was performed in the same way using the "red-driven integration" method in Example 3 except that the strain B-5318 was used instead of the strain WC196 to obtain the sfcA- or b2463-deficient strain as a mutant identified by the chroramphenicol resistance gene. The strain B-5318 in which sfcA was disrupted was designated as B-5318ΔsfcA. The strain B-5318 in which b2463 was disrupted was designated as B-5318Δb2463. A strain B-5318 with disrupted sfcA and b2463 genes, B-5318ΔsfcAΔb2463 was obtained in the same way using "red-driven integration" and the excision system method as in Example 3. The strain B-5318ΔsfcAΔb2463 was designated as B-5318Δmez.

Example 5

Evaluation of Malic Enzyme-deficient Strain

<5-1> Evaluation of L-threonine-producing Bacterium which is b2463-deficient Strain The strains B-5318Δb2463 and B-5318 were each cultured on LB agar medium (10 g/L of trypton, 5 g/L of yeast extract, 5 g/L of NaCl and 15 g/L of agar) containing 20 mg/L of streptomycin sulfate and 25 mg/L of kanamycin sulfate at 37° C. for 24 hours, and bacterial cells were taked from one-fifth of the plate and inoculated into 50 mL of LB liquid medium (10 g/L of trypton, 5 g/L of yeast extract, and 5 g/L of NaCl) containing 20 mg/L of streptomycin sulfate and 25 mg/L of kanamycin sulfate to perform preculture at 40° C. and 144 rpm for 3.5 hours.

After the completion of the preculture, the preculture broth was inoculated into 300 mL of a main culture medium contained in a 1 L-volume jar fermenter in an amount of 10% of the volume of the main culture medium to perform the main culture at 40° C. and pH 7.0. The composition of the main culture medium is shown below.

TABLE 4

[Composition of main culture medium]

| | |
|---|---|
| Glucose | 100 g/L |
| Yeast extract | 1.8 g/L |
| $FeSO_4 \cdot 7H_2O$ | 18 mg/L |
| $MnSO_4 \cdot 4H_2O$ | 18 mg/L |
| $KH_2PO_4$ | 1.0 g/L |
| $MgSO_4 \cdot 7H_2O$ | 0.36 g/L |
| $(NH_4)_2SO_4$ | 4.5 g/L |
| NaCl | 0.6 g/L |
| Streptmycin sulfate | 20 mg/L |
| Kanamycin sulfate | 25 mg/L | pH during the culture was adjusted to 7.0 by adding ammonia gas.

After the added sugar was consumed, the amount of L-threonine was measured by liquid chromatography. The results are shown in Table 5.

When the b2463-deficient strain B-5318Δb2463 was used, the threonine yield was increased compared with the control strain B-5318.

TABLE 5

| Strain | Fermentation yield of L-threonine (%) |
|---|---|
| B-5318 | 31.4 |
| B-5318Δb2463 | 32.1 |

<5-2> Evaluation of L-threonine-producing Bacterium which is sfcA-deficient Strain The strains B-5318ΔsfcA and B5318 were cultured in the same way as in <5-1>.

After the added sugar was consumed, the amount of L-threonine was measured by liquid chromatography. The results are shown in Table 6.

When the b2463-deficient strain B-5318ΔsfcA was used, the threonine yield was increased compared with the control strain B-5318.

TABLE 6

| Strain | Fermentation yield of L-threonine (%) |
|---|---|
| B-5318 | 31.4 |
| B-5318ΔsfcA | 32.2 |

<5-3> Evaluation of L-lysine-producing Bacterium which is sfcA- and b2463-deficient Strain The strains WC196, WC196ΔsfcA and WC196Δb2463 were transformed according to an ordinary method using a plasmid for lysine production which harbored dapA, dapB and dapC genes, pCABD2 (International Publication No. WO 01/53459) to obtain strains WC196/pCABD2, WC196ΔsfcA/pCABD2 and WC196Δb2463/pCABD2.

The strains WC196/pCABD2, WC196ΔsfcA/pCABD2 and WC196Δb2463/pCABD2 were cultured at 37° C. with L medium (as described below) containing 20 mg/l streptomycin until $OD_{600}$ on the medium became about 0.6. Then, an amount equivalent to the culture, of 40% glycerol solution was added to the culture. After stirring, the mixture is dispensed in appropriate aliquots and stored at −80° C. The stored aliquots are called glycerol stocks.

The glycerol stocks of the strains were thawed, and each 100 μl was uniformly spread on an L plate containing 20 mg/l streptomycin and cultured at 37° C. for 24 hours. The bacterial cells were taken from one-eighth of the obtained plate and inoculated into 20 mL of a fermentation medium (as described below) containing 20 mg/L of streptomycin to culture at 37° C. for about 16 hours by a reciprocating shaker. After the culture, amounts of lysine which had accumulated in the medium and the remaining glucose were measured by Biotech Analyzer AS210 (Sakura Seiki).

The results of L-lysine accumulation and cell-subtracted yield are shown in Table 7. The cell-subtracted yield which is a yield calculated by subtracting the amount of sugar used for bacterial cell formation, is calculated based on an assumption that 50% of consumed sugar is used for bacterial cell formation. As seen from the results, the cell-subtracted yields of the strains WC196ΔsfcA/pCABD2 and WC196Δb2463/pCABD2 increase compared that of the control strain WC196/pCABD2.

TABLE 7

| Strain | | Dry cell weight | Cell-subtracted yield |
|---|---|---|---|
| Host | Plasmid | (g/L) | (%) |
| WC196 | pCABD2 | 2.5 | 100.0 |
| WC196ΔsfcA | pCABD2 | 2.3 | 101.6 |
| WC196Δb2463 | pCABD2 | 2.2 | 104.7 |

The mediums used for evaluation of the sfcA- or b2463-deficient L-lysine-producing strain are described below. The reagents used were obtained from Wako Pure Chemicals or Nakarai Tesque unless otherwise noted. The compositions of the media used are shown below. pH was adjusted with NaOH or HCl for all media.

TABLE 8

| (L medium) | |
|---|---|
| Bacto trypton (DIFCO) | 10 g/L |
| Yeast extract (DIFCO) | 5 g/L |
| NaCl | 5 g/L |
| pH 7.0 | |
| [steam-sterilized at 120° C. for 20 minutes] | |
| (L agar medium) | |
| L medium | |
| Bacto agar (DIFCO) | 15 g/L |
| [steam-sterilized at 120° C. for 20 minutes] | |
| (L-Lysine production medium for *Escherichia* bacteria) | |
| Glucose | 40 g/L |
| Ammonium sulfate | 24 g/L |
| Potassium dihydrogen phosphate | 1.0 g/L |
| Magnesium sulfate heptahydrate | 1.0 g/L |
| Iron (II) sulfate heptahydrate | 0.01 g/L |
| Manganous sulfate tetrahydrate | 0.01 g/L |
| Yeast exatract | 2.0 g/L |
| Calcium carbonate (Pharmacopeia) | 30 g/L |

[adjusted to pH 7.0 with potassium hydroxide and steam-sterilized at 115° C. for 10 minutes provided that glucose and $MgSO_4.7H_2O$ were separately sterilized.]

Example 6

Evaluation of Malic Enzyme-deficient Strain (Δmez)

<6-1> Evaluation of L-threonine-producing Bacterium which is Malic Enzyme Deficient Strain The strains B-5318Δmez and B-5318 were each cultured on LB agar medium (10 g/L of trypton, 5 g/L of yeast extract, 5 g/L of NaCl and 15 g/L of agar) containing 20 mg/L of streptomycin sulfate and 25 mg/L of kanamycin sulfate at 37° C. for 24 hours, and bacterial cells were taken from one of the plates and suspended in 5 ml of LB liquid medium (10 g/L of trypton, 5 g/L of yeast extract, and 5 g/L of NaCl). 0.5 ml of the suspension was inoculated into 50 mL of LB liquid medium containing 20 mg/L of streptomycin sulfate and 25 mg/L of kanamycin sulfate to perform preculture at 39° C. and 144 rpm for 4 hours.

After the completion of the preculture, the preculture broth was inoculated into 300 mL of a main culture medium contained in a 1 L-volume jar fermenter in an amount of 10% of the volume of the main culture medium to perform the main culture at 39° C. and pH 7.0. The composition of the main culture medium is shown below.

TABLE 9

| [Composition of main culture medium] | |
|---|---|
| Glucose | 27 g/L |
| Yeast extract | 1.8 g/L |
| $FeSO_4.7H_2O$ | 18 mg/L |
| $MnSO_4.4H_2O$ | 18 mg/L |
| $KH_2PO_4$ | 1.5 g/L |
| $MgSO_4.7H_2O$ | 0.36 g/L |
| $(NH_4)_2SO_4$ | 4.5 g/L |
| NaCl | 0.6 g/L |
| Streptmycin sulfate | 20 mg/L |
| Kanamycin sulfate | 25 mg/L | pH during the culture was adjusted to 7.0 by adding ammonia gas.

After the added sugar was consumed and exhausted, 600 g/l aqueous glucose solution was added.

After 24-hour main culture, the amount of L-threonine was measured by liquid chromatography. The results are shown in Table 10.

When the malic enzyme-deficient strain B-5318Δmez was used, the threonine yield was increased compared with the control strain B-5318.

TABLE 10

| Strain | Fermentation yield of L-threonine (%) |
|---|---|
| B-5318 | 35.9 |
| B-5318Δmez | 38.3 |

<6-2> Evaluation of L-lysine-producing Bacterium which is Malic Enzyme-deficient Strain The strains WC196 and WC196Δmez were transformed according to an ordinary method with plasmid for lysine production, pCABD2 (International Publication No. WO 01/53459) to obtain strains WC196/pCABD2 and WC196Δmez/pCABD2.

The strains WC196/pCABD2 and WC196Δmez/pCABD2 were cultured at 37° C. with L medium (the same as used in Example 5 <5-3>) containing 20 mg/l streptomycin until $OD_{600}$ on the medium became about 0.6. Then, an amount equivalent to the culture, of 40% glycerol solution was added to the culture. After stirring, the mixture is dispensed in appropriate aliquots and stored at −80° C. The stored aliquots are called glycerol stocks.

The glycerol stocks of the strains were thawed, and each 100 µl was uniformly spread on an L plate containing 20 mg/l streptomycin and cultured at 37° C. for 24 hours. The bacterial cells were taken from one-eighth of the obtained plate and inoculated into 20 mL of a fermentation medium (the same as used in Example 5 <5-3>) containing 20 mg/L of streptomycin to culture at 37° C. for about 48 hours by a reciprocating shaker. After the culture, amounts of lysine which had accumulated in the medium and the remaining glucose were measured by Biotech Analyzer AS210 (Sakura Seiki).

The results of L-lysine accumulation and cell-subtracted yield are shown in Table 11. The cell-subtracted yield is calculated based on an assumption that 50% of consumed sugar is used for bacterial cell formation. As seen from the results, the cell-subtracted yield of the strain WC196Δmez/pCABD2 increases compared that of the control strain WC196/pCABD2.

TABLE 11

| Strain | | Dry cell weight | |
|---|---|---|---|
| Host | Plasmid | (g/L) | Cell-subtracted yield (%) |
| WC196 | pCABD2 | 5.2 | 100.0 |
| WC196Δmez | pCABD2 | 5.8 | 103.4 |

INDUSTRIAL APPLICABILITY

According to the present invention, the fermentation yield of L-lysine and/or L-threonine is increased in a method for producing L-lysine or L-threonine by fermentation using an *Escherichia* bacterium. Furthermore, the present invention can be used for breeding L-lysine and/or L-threonine-producing bacteria belonging to the genus *Escherichia*.

While the invention has been described in detail with reference to the preferred embodiments thereof, it will be apparent to one of skill in the art that various changes can be made, and equivalents employed, without departing from the scope of the invention. Each of the aforementioned documents is incorporated by reference herein in its entirety.

The invention claimed is:

1. A method for producing L-lysine or L-threonine, comprising culturing in a medium an *Escherichia* bacterium which has an ability to produce L-lysine or L-threonine, and collecting the L-lysine or L-threonine from the medium, wherein said bacterium is modified so that a gene encoding a malic enzyme is disrupted, wherein said malic enzyme is selected from the group consisting of:
   (A) a protein comprising the amino acid sequence shown in SEQ ID NO: 8, and
   (B) a protein comprising an amino acid sequence comprising substitution, deletion, insertion, or addition of one or 2 to 20 amino acid residues in the amino acid sequence shown in SEQ ID NO: 8, and wherein said protein has a malic enzyme activity.

2. The method according to claim 1, wherein said bacterium is further modified so that a gene encoding a second malic enzyme is disrupted, wherein said second malic enzyme is selected from the group consisting of:
   (A) a protein comprising the amino acid sequence shown in SEQ ID NO: 6, and
   (B) a protein comprising an amino acid sequence comprising substitution, deletion, insertion, or addition of one or 2 to 20 amino acid residues in the amino acid sequence shown in SEQ ID NO: 6, and wherein said protein has a malic enzyme activity.

3. The method according to claim 1, wherein the gene encoding the malic enzyme is a DNA selected from the group consisting of:
   (c) a DNA comprising the nucleotide sequence shown in SEQ ID NO: 7, and
   (d) a DNA which hybridizes with the nucleotide sequence shown in SEQ ID NO: 7, under stringent conditions comprising washing 1×SSC and 0.1% SDS at 60° C., and wherein said DNA encodes a protein having a malic enzyme activity.

4. The method according to claim 2, wherein the gene encoding the second malic enzyme is a DNA sequence selected from the group consisting of:
   (A) a DNA comprising the nucleotide sequence shown in SEQ ID NO: 5, and
   (B) a DNA which hybridizes with the nucleotide sequence shown in SEQ ID NO: 5 under stringent conditions comprising washing in 1×SSC and 0.1% SDS at 60° C., and wherein said DNA encodes a protein having a malic enzyme activity.

5. The method according to claim 2, wherein said malic enzymes are:
   (A) a protein comprising the amino acid sequence shown in SEQ ID NO: 6, and
   (B) a protein comprising the amino acid sequence shown in SEQ ID NO: 8.

6. The method according to claim 5, wherein the genes encoding the malic enzymes are:
(A) a DNA comprising the nucleotide sequence shown in SEQ ID NO: 5, and
(B) a DNA comprising the nucleotide sequence shown in SEQ ID NO: 7.

7. The method according to claim 5, wherein said gene is disrupted by mutating the coding region, and/or by mutating an expression control sequence of the gene.

8. The method according to claim 5, wherein the activity of said malic enzyme is attenuated due to said disruption.

9. A method for producing L-lysine or L-threonine, comprising culturing in a medium an *Escherichia coli* bacterium which has an ability to produce L-lysine or L-threonine, and collecting the L-lysine or L-threonine from the medium, wherein said bacterium is modified so that a gene encoding a malic enzyme is disrupted, wherein said malic enzyme comprises the amino acid sequence shown in SEQ ID NO: 8.

10. The method according to claim 9, wherein said gene is disrupted by mutating the coding region and/or by mutating an expression control sequence of the gene.

11. The method according to claim 9, wherein said bacterium is further modified so that a gene encoding a second malic enzyme is disrupted, wherein said second malic enzyme comprises the amino acid sequence shown in SEQ ID NO: 6.

* * * * *